US012440386B1

(12) United States Patent
Mas et al.

(10) Patent No.: US 12,440,386 B1
(45) Date of Patent: Oct. 14, 2025

(54) SLEEP MASK

(71) Applicant: TakeOffz LLC, East Point, GA (US)

(72) Inventors: Zahra Mas, East Point, GA (US); Jennifer Patton, Stone Mountain, GA (US)

( * ) Notice: Subject to any disclaimer, the term of this patent is extended or adjusted under 35 U.S.C. 154(b) by 0 days.

(21) Appl. No.: 18/388,511

(22) Filed: Nov. 9, 2023

Related U.S. Application Data

(60) Provisional application No. 63/424,849, filed on Nov. 11, 2022.

(51) Int. Cl.
*A61F 9/04* (2006.01)

(52) U.S. Cl.
CPC .................................... *A61F 9/04* (2013.01)

(58) Field of Classification Search
CPC .............. A61F 9/04; A61F 9/02; A61F 9/027; A41D 13/1184; A41D 13/1161; A61B 6/107; A45D 44/002; G02C 3/003
See application file for complete search history.

(56) References Cited

U.S. PATENT DOCUMENTS 1,553,010 A 9/1925 Terry et al.
1,743,801 A 1/1930 Reynolds
1,799,064 A * 3/1931 Rickerd .................... A61F 9/02 2/12
1,807,475 A 5/1931 Gibson
1,886,725 A * 11/1932 Pedersen .................. A61F 9/04 604/308
1,924,315 A 8/1933 Hemphill et al.
2,165,668 A 7/1939 Vaccaro
2,191,937 A 2/1940 Low
2,233,600 A 3/1941 Glasberg
2,305,080 A * 12/1942 Hemphill ................. A61F 9/04 2/15
2,537,768 A 1/1951 Laporte
2,543,104 A 2/1951 Golding
2,671,446 A 3/1954 Mann
2,671,898 A 3/1954 Wade
2,874,385 A 2/1959 Wade
2,891,252 A 6/1959 Lazo
(Continued)

OTHER PUBLICATIONS

Screenshot of google image search results of phrase, “sleep mask do no disturb”; conducted Oct. 3, 2022.
(Continued)

*Primary Examiner* — Jillian K Pierorazio
(74) *Attorney, Agent, or Firm* — Eric Kelly

(57) ABSTRACT

A sleep mask with an opaque first-portion (face-covering-portion) is configured to removably cover over the eyes of a wearer of the sleep mask and includes at least one moldable-member that is configured to allow the opaque first-portion to be molded to conform to the exterior geometry of the wearer’s face (e.g., around the eyes) and the at least one moldable-member is also configured to allow ear-loops of the sleep mask to be molded to conform to shapes and geometry of the wearer’s ears. The ear-loops of the sleep mask are not elastic and do not exert force and/or pressure upon the ears as would elastic ear loops. Further, the sleep mask includes at least one removable label that includes messaging. The label may be removably attach (or detach) from an exterior front of the sleep mask, depending upon if the wearer wants to present the message or not.

20 Claims, 21 Drawing Sheets

(56) References Cited

U.S. PATENT DOCUMENTS

| | | | | | |
|---|---|---|---|---|---|
| 2,942,270 | A | | 6/1960 | Enright | |
| D251,576 | S | | 4/1979 | Geenen-Megens | |
| D272,865 | S | | 3/1984 | Edelmann | |
| 4,649,908 | A | | 3/1987 | Ghlay | |
| D292,410 | S | | 10/1987 | Hunter | |
| 4,790,031 | A | | 12/1988 | Duerer | |
| D302,167 | S | * | 7/1989 | Sherman | D16/301 |
| 4,872,217 | A | * | 10/1989 | Kitayama | A61F 9/04 2/15 |
| D309,465 | S | | 7/1990 | Russell | |
| D313,125 | S | | 12/1990 | Gordon | |
| D319,449 | S | | 8/1991 | Millar | |
| D344,283 | S | | 2/1994 | Russell | |
| 5,343,561 | A | | 9/1994 | Adamo | |
| D365,918 | S | * | 1/1996 | Izegbu | D2/894 |
| D374,950 | S | | 10/1996 | Clark | |
| D388,812 | S | | 1/1998 | Miehe et al. | |
| 5,818,569 | A | * | 10/1998 | Berent | A61F 9/027 2/452 |
| D410,021 | S | | 5/1999 | Heyman et al. | |
| 5,940,886 | A | | 8/1999 | McCarthy Smith | |
| D457,908 | S | | 5/2002 | Lane et al. | |
| D465,234 | S | | 11/2002 | Gordon | |
| 6,543,056 | B2 | * | 4/2003 | Spiteri | A61F 9/04 2/15 |
| D478,342 | S | | 8/2003 | Magidson | |
| D481,748 | S | | 11/2003 | Magidson | |
| D485,854 | S | | 1/2004 | Thomason | |
| D489,749 | S | | 5/2004 | Landvik | |
| D548,265 | S | | 8/2007 | Lane et al. | |
| D592,236 | S | | 5/2009 | McGrath | |
| D639,441 | S | | 6/2011 | Sferle | |
| D668,703 | S | | 10/2012 | Gordon et al. | |
| D693,062 | S | | 11/2013 | Bowen et al. | |
| D694,309 | S | | 11/2013 | Shelledy | |
| D694,804 | S | | 12/2013 | Horvat | |
| 8,852,073 | B2 | | 10/2014 | Genereux et al. | |
| D717,362 | S | | 11/2014 | Kaufer | |
| D722,727 | S | | 2/2015 | Maruyama et al. | |
| D723,740 | S | | 3/2015 | Jenkins | |
| 8,966,662 | B2 | | 3/2015 | Belliappa | |
| D726,244 | S | | 4/2015 | Defranco | |
| 9,168,177 | B2 | | 10/2015 | Valentino | |
| 9,186,276 | B2 | | 11/2015 | Parziale | |
| D771,179 | S | | 11/2016 | Harris | |
| 9,522,084 | B2 | | 12/2016 | Wilson | |
| D777,824 | S | | 1/2017 | DeMarie | |
| 9,572,718 | B2 | | 2/2017 | Sternlight | |
| 9,707,409 | B2 | | 7/2017 | Colbaugh | |
| 10,021,954 | B2 | | 7/2018 | Wardaszka | |
| D830,448 | S | | 10/2018 | Hardi | |
| 10,285,862 | B2 | | 5/2019 | Belliappa | |
| D854,075 | S | | 7/2019 | Carver | |
| 10,349,177 | B2 | | 7/2019 | Hanson | |
| D861,060 | S | | 9/2019 | Zheng | |
| 10,406,035 | B1 | * | 9/2019 | Scott | A61F 9/04 |
| D861,771 | S | | 10/2019 | Schwarz et al. | |
| D861,772 | S | | 10/2019 | Lian | |
| D862,568 | S | | 10/2019 | Holtz et al. | |
| 10,426,666 | B1 | | 10/2019 | Seidenfeld et al. | |
| D867,436 | S | | 11/2019 | Lian | |
| D867,437 | S | | 11/2019 | Lian | |
| D876,642 | S | | 2/2020 | Michalak et al. | |
| D887,484 | S | | 6/2020 | Guo | |
| D889,529 | S | | 7/2020 | Guo | |
| D906,405 | S | | 12/2020 | Seidenfeld et al. | |
| D906,633 | S | | 1/2021 | Paradise | |
| D907,688 | S | | 1/2021 | Du | |
| D911,429 | S | | 2/2021 | Guo | |
| D918,991 | S | | 5/2021 | Du | |
| D939,617 | S | | 12/2021 | Liu | |
| 11,191,672 | B2 | | 12/2021 | Lombardo | |
| 11,197,782 | B2 | | 12/2021 | Belliappa | |
| D940,874 | S | | 1/2022 | Edwards | |
| D949,954 | S | | 4/2022 | Sitt et al. | |
| D954,133 | S | | 6/2022 | Chen | |
| D954,134 | S | | 6/2022 | Johnson et al. | |
| D954,795 | S | | 6/2022 | Lian | |
| D957,511 | S | | 7/2022 | Liu | |
| D957,512 | S | | 7/2022 | Liu | |
| D958,233 | S | * | 7/2022 | Cheng | D16/301 |
| D960,226 | S | | 8/2022 | Lu | |
| D960,967 | S | | 8/2022 | Chen | |
| D963,031 | S | | 9/2022 | Liu | |
| 11,766,359 | B1 | * | 9/2023 | Shaner, Sr. | A61F 9/04 2/15 |
| 2002/0138891 | A1 | | 10/2002 | Spiteri | |
| 2003/0056281 | A1 | | 3/2003 | Hasegawa | |
| 2003/0079266 | A1 | | 5/2003 | Magidson | |
| 2005/0229281 | A1 | * | 10/2005 | Glasser | A61F 9/04 2/15 |
| 2006/0143766 | A1 | * | 7/2006 | Ramsey | A61F 9/02 2/15 |
| 2010/0122398 | A1 | * | 5/2010 | Luciano | A61F 9/04 2/173 |
| 2014/0041091 | A1 | | 2/2014 | Sternlight | |
| 2014/0331383 | A1 | | 11/2014 | Bially | |
| 2015/0173487 | A1 | * | 6/2015 | Wardaszka | A61F 9/04 604/303 |
| 2016/0008175 | A1 | | 1/2016 | Bergman et al. | |
| 2016/0022045 | A1 | * | 1/2016 | Lee | A61F 9/04 112/475.08 |
| 2016/0262936 | A1 | | 9/2016 | Belliappa | |
| 2019/0231595 | A1 | | 8/2019 | Holtz et al. | |
| 2022/0087867 | A1 | | 3/2022 | Bamberg | |
| 2023/0104958 | A1 | * | 4/2023 | Markelz | A41D 13/1184 132/319 |

OTHER PUBLICATIONS

Screenshot of google image search results of phrase, “sleep mask with message”; conducted Oct. 3, 2022.

* cited by examiner

SLEEP MASK

PRIORITY NOTICE

The present application claims priority under 35 U.S.C. § 119(e) to U.S. Provisional Patent Application Ser. No. 63/424,849 filed on Nov. 11, 2022, the disclosure of which is incorporated herein by reference in its entirety.

TECHNICAL FIELD OF THE INVENTION

The present invention relates in general to face masks and more specifically to face masks that are sleep masks and/or travel masks that are configured to cover over the eyes during use to facilitate sleep, resting, and/or relaxation of the wearer.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Circa 2022 prior art sleep masks continue to suffer from some problems. Prior art sleep masks that may tend to stay on and in proper place over the eyes of a sleeping person while that person is laying prone on their back may tend to fall off if that person was sleeping sitting upright. Sleeping while sitting upright is very common under certain situations, such as, but not limited to, sleeping on: airlines, airplanes, planes, trains, trams, buses, cars, trucks, vans, RVs (recreational vehicles), motor vehicles, boats, vessels, ferries, airships, flying vehicles, or anywhere where a person may be seated.

Some prior art sleep masks have tried to solve the problem of falling off while sleeping sitting up by more securely attaching the given prior art sleep mask to the person's ears, for example, by using elastic ear straps. However, this is undesirable as elastic straps on the ears becomes very quickly uncomfortable and often results in pressure bruising where the elastic contacted the skin and/or squeezed against the skin.

It would be desirable to have a sleep mask that is configured for use while a sleeping person is sitting upright, i.e., tends to not fall off while in this position, but does so without exerting uncomfortable pressure upon the sleeping person's ears, such as, but not limited to, not using elastic or the like ear loops/straps that unnecessarily squeeze the ears of the wearer.

It would be desirable to have a sleep mask that is configured for use while a sleeping person is sitting upright, i.e., tends to not fall off while in this position, and does so by including at least one moldable element/member (in, of, and/or associated with the ear loops) such that the sleep mask may easily conform to the exterior geometry of a person's face to minimize falling off from the face; and/or to use such an at least one moldable element/member within the ear loops as well that is non-elastic so as to not exert undue force (pressure) upon the ears.

Further, most prior art sleep masks do not include any messaging on their exteriors. However, when one is sleeping in a sitting position in a seat, that person may be in public and/or amongst other people and it may be desirable to include some messaging on an exterior of that sleep mask, such as, but not limited to, a message to not disturb the sleeping person or to awake the sleeping person upon certain conditions. Some prior art sleep masks have responded to this need by including such messaging. However, it would be desirable if such messaging could be removable, such that the messaging could be presented when desired or removed when desired to not present any such messaging. Thus, it would be desirable if such messaging was implemented in a removable manner and/or that includes a variety (plurality) of different messages allowing the wearer to pick a suitable removable message for a particular use case situation when so desired.

There is a need in the art for such sleep masks, i.e., sleep masks that include at least one moldable element/member for both molding to a person's face and to mold to the ears in a non-elastic manner; that includes removable messaging; and/or that includes an ability to choose from a variety of different messages.

It is to these ends that the present invention has been developed.

BRIEF SUMMARY OF THE INVENTION

To minimize the limitations in the prior art, and to minimize other limitations that will be apparent upon reading and understanding the present specification, embodiments of the present invention describe sleep masks or more specifically travel sleep masks. In some embodiments, a sleep mask may comprise an opaque first-portion (e.g., a face-covering-portion) that may be configured to removably cover over the eyes of a wearer of that sleep mask and thus providing a dark environment to the eyes of the wearer that is conducive for sleep, rest, and/or relaxation. In some embodiments, this sleep mask may further comprise at least one (elongate) moldable-member that is configured to allow the opaque first-portion (the face-covering-portion) to be molded to conform to the exterior geometry of the wearer's face (e.g., around the eyes region of the wearer), wherein this molding of the first-portion (the face-covering-portion) may help to keep the sleep mask from falling off of the wearer, and/or minimize undesired exterior visible light from reaching the eyes of the wearer, when the sleep mask is being removably worn as intended. In some embodiments, the at least one (elongate) moldable-member may also be configured to allow two (2) opposing ear-loops of the sleep mask to be molded to conform to a shape of the wearer's ears, wherein this molding of the ear-loops also helps to keep the sleep mask from falling off of the wearer. In some embodiments, the ear-loops of the sleep mask are not elastic and do not exert undue force and/or pressure upon the ears as would elastic ear loops common in prior art sleep masks. Further, the sleep mask may comprise at least one removable label that includes messaging or may comprise a plurality of removable labels each with a different message. In some embodiments, the at least one removable label may be removably attach (or detach) from an exterior front of the sleep mask, depending upon if the wearer wants to present a given message or not. Example messaging may comprise (written) content that the wearer does not wish to be disturbed or that the wearer wants to be awoken upon certain conditions (such as, but not limited to, when arriving at a destination, when cruising, when in-flight, and/or the like).

Such a sleep mask is configured for non-falling off sleeping use of the wearer when the wearer is sitting upright, such as, in a seat, chair, sofa, and/or the like. Such a sleep mask is configured for non-falling off sleeping use of the wearer when the wearer is sitting upright on/in an airplane, plane, train, tram, bus, car, truck, van, RV (recreational vehicle), motor vehicle, boat, vessel, ship, ferry, airship, flying vehicle, or anywhere where a person may be seated (including merely sitting on a floor or the ground). Such a sleep mask may of course be readily used while the wearer is in a different position (e.g., other than sitting), such as, but not limited to, the wearer being prone (laying down).

It is an objective of the present invention to provide a sleep mask that is configured to not fall off the wearer when the wearer is sleeping upright.

It is another objective of the present invention to provide a sleep mask that is configured to not fall off the wearer when the wearer is sleeping in a seated position.

It is another objective of the present invention to provide a sleep mask that is configured to not fall off the wearer when the wearer is sleeping and sitting.

It is another objective of the present invention to provide a sleep mask that is configured to not fall off the wearer during sleeping use on airlines, airplanes, planes, trains, trams, buses, cars, trucks, vans, RVs (recreational vehicles), motor vehicles, boats, vessels, ships, ferries, airships, flying vehicles, or anywhere where a person may be seated.

It is another objective of the present invention to provide a sleep mask that is configured to function as a sleep mask to use while traveling (e.g., when the wearer may be a passenger).

It is another objective of the present invention to provide a sleep mask that is easy to use.

It is another objective of the present invention to provide a sleep mask that is easy to manufacture.

It is another objective of the present invention to provide a sleep mask that is relatively inexpensive to manufacture.

It is another objective of the present invention to provide a sleep mask that is fast to manufacture.

It is another objective of the present invention to provide a sleep mask that may be custom colored to match colored branding of a business, organization, and/or institution that intends to use such sleep masks (such as, but not limited to, a given airline).

It is another objective of the present invention to provide a sleep mask that is comfortable to wear.

It is another objective of the present invention to provide a sleep mask that does not exert undue force and/or pressure upon the ears of the wearer by not having elastic (or the like) ear-loops.

It is another objective of the present invention to provide a sleep mask that is moldable to conform to the wearer's external face geometry.

It is another objective of the present invention to provide a sleep mask that is moldable to conform to the wearer's ear's shape.

It is another objective of the present invention to provide a sleep mask that includes at least one moldable-member (element) that provides the moldable functionality of the sleep mask.

It is another objective of the present invention to provide a sleep mask that includes at least one moldable-member (element) that is easy for the wearer to mold, without using any tools other than the wearer's hand(s), and wherein a given molded shaped is retained until changed by the wearer.

It is another objective of the present invention to provide a sleep mask that includes at least one moldable-member (element) that allows the sleep mask to be shaped into a relatively small compact configuration for when the sleep mask is not being removably worn on the face of the wearer.

It is another objective of the present invention to provide a sleep mask that includes at least one removable label.

It is another objective of the present invention to provide a sleep mask that includes a plurality of removable labels.

It is another objective of the present invention to provide a sleep mask where attachment means between the sleep mask and a given label may be accomplished using one or more of: a plurality of hooks fastener, a plurality of loops fastener, Velcro, a Nomax fastener, snaps, buttons, a zipper, a magnet, a ferrous metal, a magnetic strip, a ferrous metal strip, a clip, a fastener, a mechanical fastener, a portion thereof, combinations thereof, and/or the like.

It is another objective of the present invention to provide a sleep mask that includes at least one removable label that is removably attachable to a front exterior of the sleep mask.

It is another objective of the present invention to provide a sleep mask that includes at least one removable label that includes messaging.

It is another objective of the present invention to provide a sleep mask that includes a plurality of removable labels that includes a variety of different messages.

It is another objective of the present invention to provide a sleep mask wherein the messaging from removable label(s) is at least in written textual form.

It is another objective of the present invention to provide a sleep mask that includes at one removable label that includes messaging, wherein the messaging conveys a message that the wearer wishes to not be disturbed.

It is yet another objective of the present invention to provide a sleep mask that includes at one removable label that includes messaging, wherein the messaging conveys a message that the wearer wants to be awoken upon certain conditions (such as, but not limited to, when arriving at a destination, when cruising, when in-flight, and/or the like).

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

(FIG. 4 and FIG. 3 show the second-portions [ear-loops] in different positions/configuration from each other).

(FIG. 18 and FIG. 17 are from similar but different viewing angles).

REFERENCE NUMERAL SCHEDULE

Figure 1:
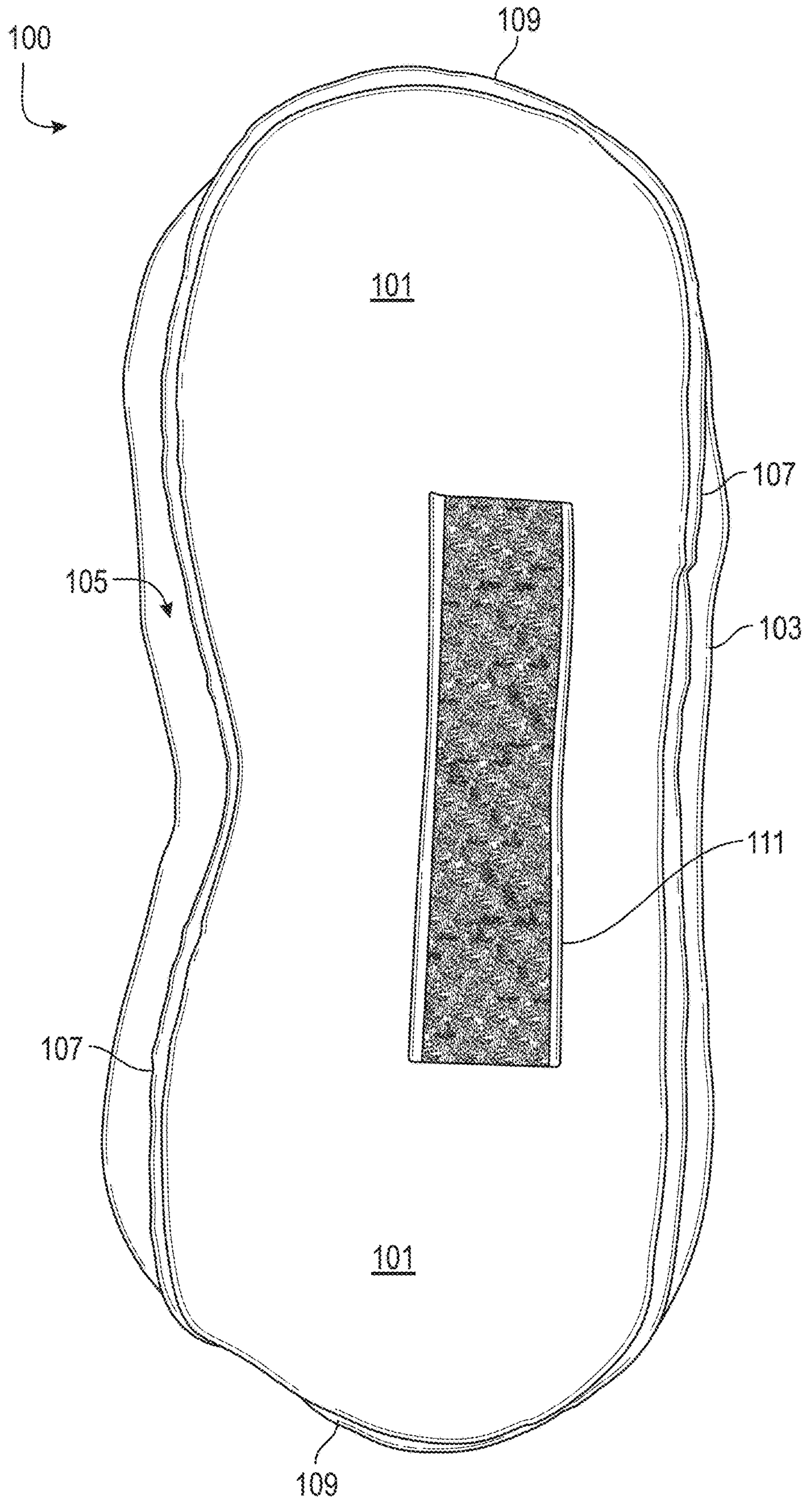
FIG. 1 shows a front view of a sleep mask that shows a front-exterior of that sleep mask.

100 sleep mask 100
101 front-exterior (planar-member) 101
103 top-perimeter 103
105 bottom-perimeter 105
107 piping 107
109 side-perimeter 109
111 label-attachment-means 111
201 first-portion (face-covering-portion) 201
203 second-portion (ear-loop) 203
205 ear-loop-covering (ear-loop-cover) 205
206 cutaway section 206
207 moldable-member 207
301 face-facing-panel (planar-member) 301
901 hand 901
1401 label 1401
1403 messaging 1403
1501 terminal end 1501
1503 thickness (diameter) 1503
1601 uncut moldable-member 1601
1700 wearer 1700
1701 face 1701
1703 ear 1703
1705 nose 1705
1901 label (for sleep mask) 1901
**1901*a* label (for sleep mask) 1901*a***
**1901*b* label (for sleep mask) 1901*b***
**1901*c* label (for sleep mask) 1901*c***
**1901*d* label (for sleep mask) 1901*d***
1903 front-of-label (messaging) 1903
**1903*a* front-of-label (messaging) 1903*a***
**1903*b* front-of-label (messaging) 1903*b***
**1903*c* front-of-label (messaging) 1903*c***
**1903*d* front-of-label (messaging) 1903*d***
1905 back-of-label (attachment-means of a label) 1905
1907 plurality of labels 1907

DETAILED DESCRIPTION OF THE INVENTION

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

Figure 4:
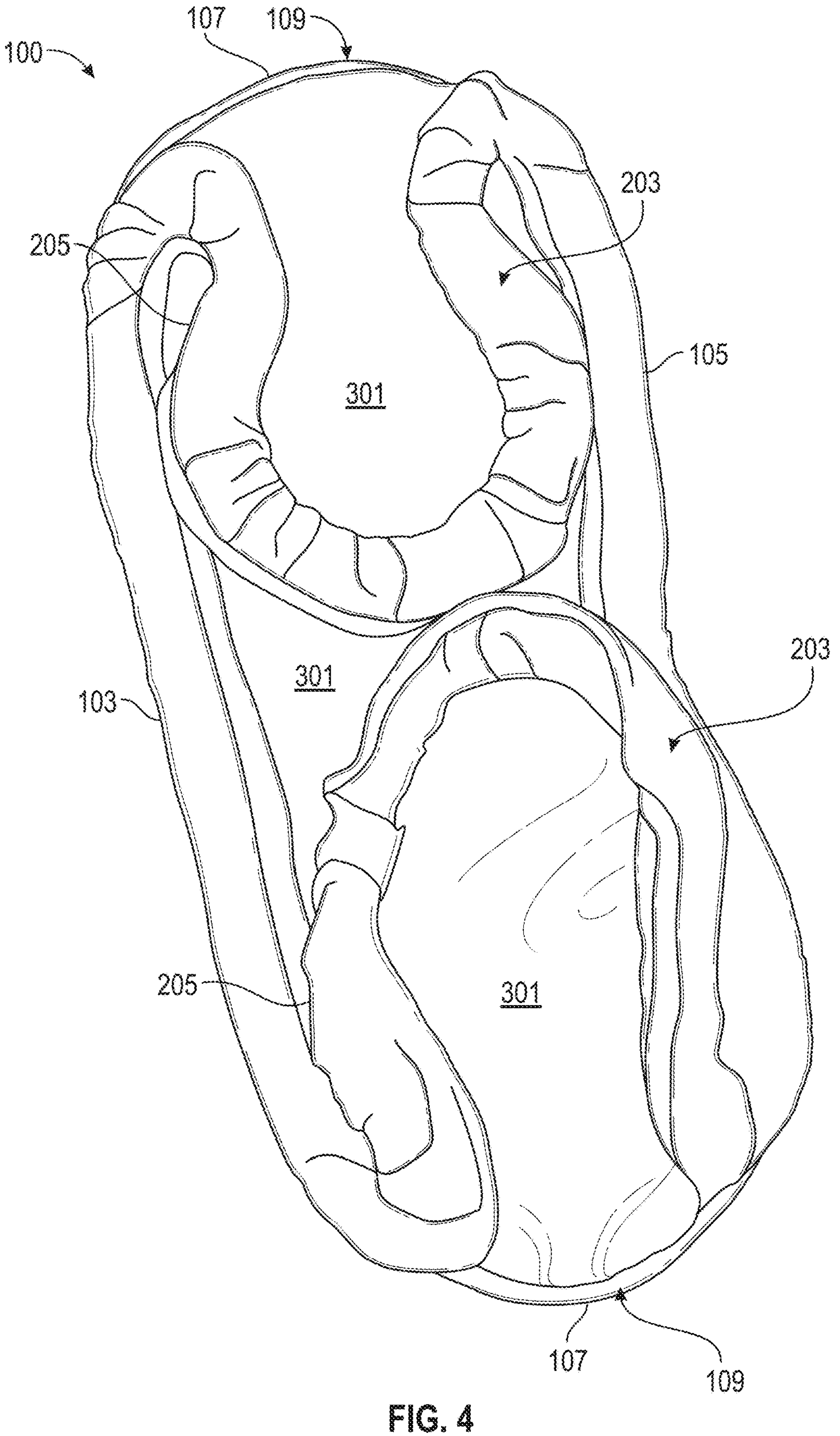
FIG. 4 shows a back (rear) view of the sleep mask from FIG. 1.

FIG. 1 shows a front view of a sleep mask 100 that shows a front-exterior 101 of that sleep mask 100. In some embodiments, sleep mask 100 may be configured to be removably worn over a face 1701 of a wearer 1700 (see e.g., FIG. 17 for wearer 1700 and face 1701), with at least a first-portion 201 covering over the eyes of the wearer 1700 and at least partially conforming to an exterior geometry of the face 1701 of the wearer 1700. In some embodiments, sleep mask 100 may be configured to be removably worn over a face 1701 of a wearer 1700, with at least a second-portion 203 (ear-loop 203) configured for removable engagement to each ear 1703 (see e.g., FIG. 17 for ear 1703) of the wearer 1700 to help keep the 100 removably worn on the face 1701 of the wearer 1700. In some embodiments, when sleep mask 100 may be removably worn over the eyes (face 1701) of the wearer 1700, sleep mask 100 may be configured promote rest or sleep of the wearer 1700. In some embodiments, the at least the first-portion 201 may be at least substantially (mostly) non-transparent, non-translucent, opaque, non-see-through, not clear, portions thereof, combinations thereof, and/or the like, with respect to light that is typically referenced as visible light to humans. Note, front-exterior 101 shown in FIG. 1 is a component of the at least the first-portion 201. Note, in FIG. 1 the second-portions 203 (ear-loops 203) are not shown, but are instead folded beneath front-exterior 101 as shown in FIG. 4.

FIG. 1 also shows top-perimeter 103, bottom-perimeter 105, piping 107, side-perimeter 109, and label-attachment-means 111 of sleep mask 100. In some embodiments, the at least the first-portion 201 may comprise front-exterior 101, top-perimeter 103, bottom-perimeter 105, piping 107, side-perimeter 109, label-attachment-means 111, and face-facing-panel 301 (see FIG. 3 for face-facing-panel 301). In some embodiments, the at least the first-portion 201 may not comprise the second-portions 203 (ear-loops 203).

Continuing discussing FIG. 1, in some embodiments, front-exterior 101 may be an at least substantially (mostly) flat and/or planar member/surface that is exterior, i.e., that faces away from the face 1701 of the wearer 1700 when sleep mask 100 is being removably worn by the wearer 1700. In some embodiments, front-exterior 101 may be comprised of at least one fabric. In some embodiments, the at least one fabric of front-exterior 101 may be one or more of: natural, synthetic, soft, flexible, pliable, bendable, foldable, non-elastic, washable, machine washable, cleanable, wipeable, sterilizable, portions thereof, combinations thereof, and/or the like. In some embodiments, front-exterior 101 may be have a 2D (two-dimensional) shape that is configured to removably cover over both eyes of the wearer 1700. In some embodiments, front-exterior 101 may be longer than wide, and wider than thick. In some embodiments, the width of front-exterior 101 may be variable along the length of front-exterior 101. In some embodiments, the width of front-exterior 101 may be wider at the portions of front-exterior 101 that may removably cover over the eyes of the wearer 1700 and narrower at the portion of front-exterior 101 that rests on or above a bridge of a nose 1705 of the wearer 1700. In some embodiments, the thickness of front-exterior 101 may be uniform (or at least mostly/substantially uniform). In some embodiments, front-exterior 101 may not be polygon shaped.

Continuing discussing FIG. 1, in some embodiments, a top length of front-exterior 101 may be bounded by top-perimeter 103. In some embodiments, a bottom length of front-exterior 101 may be bounded by bottom-perimeter 105. In some embodiments, along at least most of the length of front-exterior 101, top-perimeter 103 and bottom-perimeter 105 may be separated from each other by the (variable) width of front-exterior 101. In some embodiments, top-perimeter 103 and bottom-perimeter 105 may be covered by at least one fabric, which may be the same at least one fabric of front-exterior 101 or a different fabric. In some embodiments, the at least one fabric of top-perimeter 103 and bottom-perimeter 105 may be one or more of: natural, synthetic, soft, flexible, pliable, bendable, foldable, non-elastic, washable, machine washable, cleanable, wipeable, sterilizable, portions thereof, combinations thereof, and/or the like. In some embodiments, contained within top-perimeter 103 and bottom-perimeter 105 may be at least one moldable-member 207 (partially shown in FIG. 2).

Continuing discussing FIG. 1, in some embodiments, running just (immediately) below top-perimeter 103 may be a portion of piping 107; and running just (immediately) above bottom-perimeter 105 may be another portion of piping 107. In some embodiments, piping 107 may be piping of sleep mask 100, as piping is generally understood in the garment, clothing, apparel, and/or textiles industries. In some embodiments, at least one strip and/or band of piping 107 may generally run around an exterior perimeter (or just inside portions of that perimeter of front-exterior 101. In some embodiments, piping 107 may be attached to front-exterior 101. In some embodiments, piping 107 may be attached to front-exterior 101 by one or more of seam(s), stitches, stitching, weld, welding, ultrasonic weld, ultrasonic welding, adhesive, glue, gluing, epoxy, portions thereof, combinations thereof, and/or the like.

Continuing discussing FIG. 1, in some embodiments, there may be two (2) opposing side-perimeters 109 that may be at least mostly (substantially) separated from each other by lengths of the top-perimeter 103 and the bottom-perimeter 105. In some embodiments, a full perimeter and/or exterior 2D boundary of front-exterior 101 may be defined by top-perimeter 103, then one side-perimeter 109, then bottom-perimeter 105, then the remaining side-perimeter 109, and then back to the top-perimeter 103. In some embodiments, two opposing portions of piping 107 may coincide (e.g., be colinear) with each side-perimeter 109.

Continuing discussing FIG. 1, in some embodiments, attached to at least a portion of front-exterior 101 may be a label-attachment-means 111. In some embodiments, attached to a middle region of front-exterior 101 may be label-attachment-means 111. In some embodiments, label-attachment-means 111 may be configured for removable attachment to a label 1401. In some embodiments, label 1401 may be configured for removable attachment to label-attachment-means 111. In some embodiments, label-attachment-means 111 may be region of: a Nomax fastener, Velcro, a plurality of hooks, a plurality of loops, or the like fabric backed fastener that is attached (affixed) to the at least the portion of front-exterior 101. In some embodiments, when label-attachment-means 111 may be a plurality of hooks, then label-attachment-means 111 may be configured to be removably attached to label 1401, wherein a backside 1905 of label 1401 may have complementary plurality of loops for removable attachment to the plurality of hooks of label-attachment-means 111. Or alternatively, in some embodiments, when label-attachment-means 111 may be a plurality of loops, then label-attachment-means 111 may be configured to be removably attached to label 1401, wherein the backside 1905 of label 1401 may have complementary plurality of hooks for removable attachment to the plurality of loops of label-attachment-means 111. See e.g., FIG. 14A and FIG. 14B for label 1401 and its removable attachment to label-attachment-means 111 of front-exterior 101; and see FIG. 19 for a back (rear) 1905 of a given label. In some embodiments, label-attachment-means 111 may be selected from one or more of: a Nomax fastener, a Velcro fastener, a plurality of hooks fastener, a plurality of loops fastener, snaps, buttons, a zipper, a magnet, a ferrous metal, a magnetic strip, a ferrous metal strip, a clip, a fastener, a mechanical fastener, portions thereof, combinations thereof, and/or the like. In some embodiments, a type and/or style of label-attachment-means 111 may be selected in order to be complementary with attachment-means 1905. In some embodiments, a type and/or style of label-attachment-means 111 and/or of attachment-means 1905 may be selected in order to be complementary with each other to facilitate removable attachment of the given label from/to label-attachment-means 111 of a given sleep mask 100. See FIG. 19 for attachment-means 1905 on a back (rear) 1905 of a given label.

Figure 2:
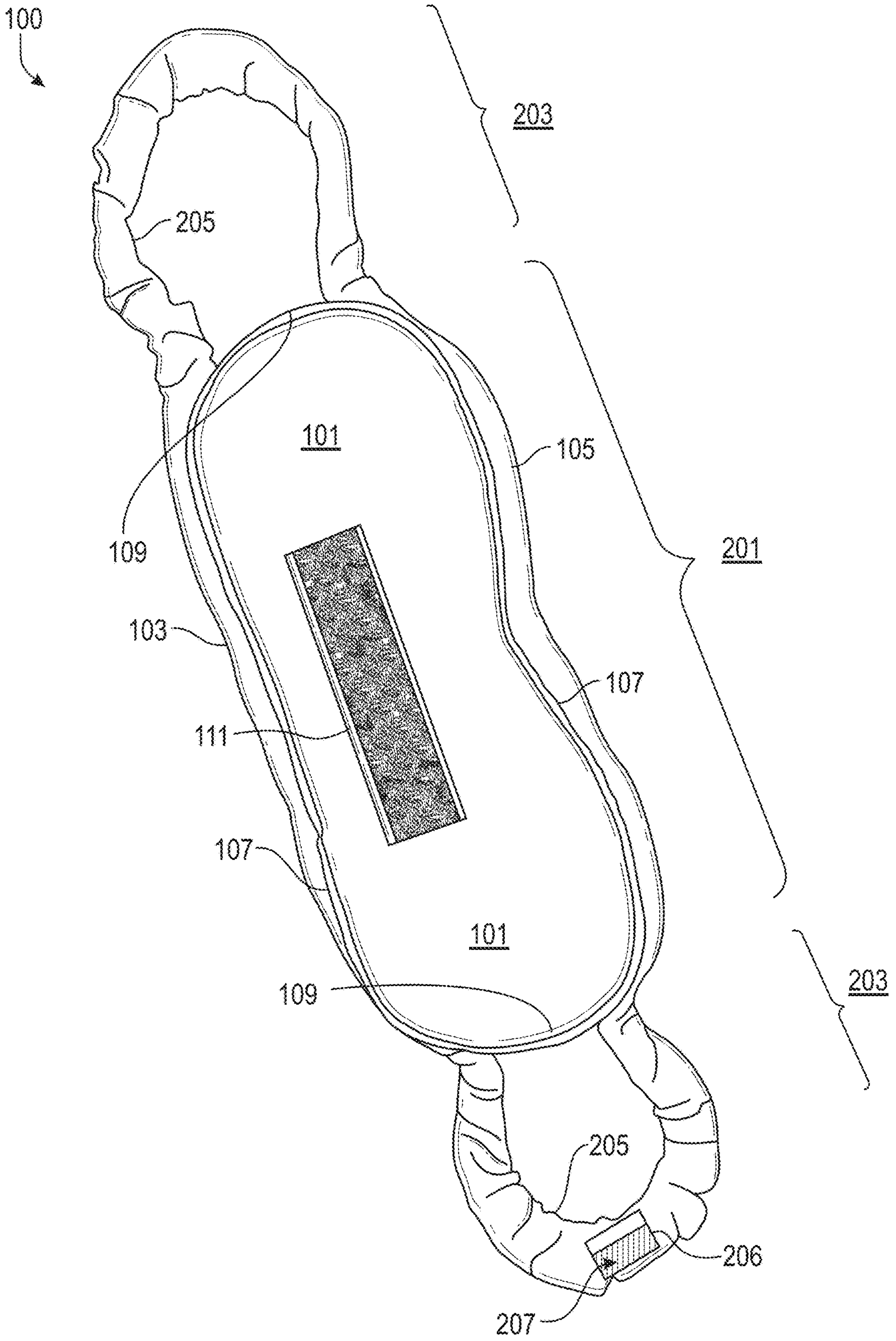
FIG. 2 shows a front view of the sleep mask from FIG. 1, that is similar to the front view of FIG. 1, except in FIG. 2, second-portions (ear-loops) of the sleep mask are unfolded from a first-portion of the sleep mask, such that the second-portions (ear-loops) are shown visible in this front view of FIG. 2.

FIG. 2 shows a front view of sleep mask 100 that is similar to the front view of FIG. 1, except in FIG. 2, the second-portions 203 (ear-loops 203) are unfolded from the first-portion 201, such that the second-portions 203 (ear-loops 203) are shown visible in this front view of FIG. 2. As compared to FIG. 1, FIG. 2 more clearly shows the delineation between first-portion 201 and the second-portions 203 (ear-loops 203). In some embodiments, the at least the first-portion 201 may comprise front-exterior 101, top-perimeter 103, bottom-perimeter 105, piping 107, side-perimeter 109, label-attachment-means 111, and face-facing-panel 301. In some embodiments, the at least the first-portion 201 may not comprise the second-portions 203 (ear-loops 203).

As shown in FIG. 2, the top-perimeter 103 and the bottom-perimeter 105 of one side (e.g., left side) of the sleep mask 100 may flow/transition into one ear-loop 203; and the top-perimeter 103 and the bottom-perimeter 105 of the other side (e.g., right side) of the sleep mask 100 may flow/transition into the other ear-loop 203. In some embodiments, ear-loops 203 may be at least substantially (mostly) non-elastic and/or non-stretchy with respect to a human applying tension to the given ear-loop 203. In some embodiments, during normal and intended removable wearing of sleep mask 100 on the face 1701 of the wearer 1700, each ear-loop 203 may at least substantially surround a given ear 1703 of the wearer 1700, and portions of each ear-loop 203 may rest on top of the ears 1703 of the wearer 1700.

Continuing discussing FIG. 2, in some embodiments, each ear-loop 203 may be covered by an ear-loop-covering 205. In some embodiments, each ear-loop-covering 205, top-perimeter 103, and bottom-perimeter 105 may be a flexible elongate hollow sleeve that is configured to house a portion of moldable-member 207. In some embodiments, each ear-loop-covering 205 may be at least one fabric. In some embodiments, the at least one fabric of each ear-loop-covering 205 may be the same or different with respect to the least one fabric of front-exterior 101, top-perimeter 103, and/or bottom-perimeter 105. In some embodiments, the at least one fabric of each ear-loop-covering 205 may be one or more of: natural, synthetic, soft, flexible, pliable, bendable, foldable, non-elastic, washable, machine washable, cleanable, wipeable, sterilizable, portions thereof, combinations thereof, and/or the like.

FIG. 2 shows a portion of ear-loop-covering 205 removed 206 (cut-away 206) from one ear-loop-covering 205 to show a portion of moldable-member 207 that is located within and runs within ear-loop-coverings 205. In some embodiments, moldable-member 207 may be located within: top-perimeter 103, bottom-perimeter 105, and the two ear-loops 203. However, in some embodiments, moldable-member 207 may be entirely absent (missing) from side-perimeter(s) 109 of a given sleep mask 100. In some embodiments, moldable-member 207 may be bendable, malleable, foldable, sculptable, and/or the like in a manner that moldable-member 207 retains its shape after such bending (articulation) without any external forces acting on moldable-member 207 (aside from the local and normal gravitational field of the Earth), i.e., a particular bent shape of moldable-member 207 may be self-supporting. In some embodiments, moldable-member 207 may be configured to be bent, formed, folded, unfolded, sculpted, articulated, and/or the like by a single human only using their hands and/or fingers without using any external tools. In some embodiments, the bendable, malleable, foldable, sculptable, and/or the like nature of moldable-member 207 allows the first-portion 201 to be molded into a shape that comfortably conforms to the exterior shape of the face 1701 of the wearer 1700. In some embodiments, the bendable, malleable, foldable, sculptable, and/or the like nature of moldable-member 207 allows the ear-loops 203 to be molded into a shape that comfortably conforms to the exterior shape of the ears 1703 of the wearer 1700 and without exerting an unconformable force on the ears 1703 as occurs with elastic ear straps of prior art sleep masks. In some embodiments, moldable-member 207 may be at least mostly (substantially) non-elastic and non-stretchy with respect to a human applying tension to moldable-member 207. See FIG. 15 for moldable-member 207 by itself, without other elements of sleep mask 100 being shown. And see FIG. 16 for uncut moldable-member 1601 which is a precursor to moldable-member 207 before moldable-member 207 is cut to size for use in a given sleep mask 100.

In some embodiments, moldable-member 207 may be self-supporting. In some embodiments, moldable-member 207 may be (repeatably) bent, articulated, folded, shaped, contoured, and/or the like into a variety of different shapes, that once formed may be self-supporting (self-maintaining), i.e., once a given shape of moldable-member 207 has been formed (e.g., by flexing, bending, articulation, folding, shaping, contouring, and/or the like), that particular formed shaped may maintain itself without outside (external) forces being applied to sleep mask 100 and/or to moldable-member 207; and that is how "self-supporting" may be defined as used herein. For example, if a particular bent shape of moldable-member 207 (and/or sleep mask 100) was dropped in freefall through Earth's atmosphere (or through vacuum) (e.g., with no or minimal wind) that particular bent shape would be at least substantially (mostly) maintained. And/or, in some embodiments, "self-supporting" in this context (and as used herein) may mean if a person (or tool) were to hold one (terminal) end of moldable-member 207 and regardless of a particular bent shape for that moldable-member 207, and if no other portion of moldable-member 207 was physically being supported, that whatever shape of moldable-member 207 may be in, that shape would be maintained.

In some embodiments, moldable-member 207 may comprise at least one elongate-member that is fixed, finite, non-variable, non-extendable, non-telescoping, and/or predetermined with respect to an overall length, outside diameter (gauge), and/or the like, of that particular moldable-member 207. However, such parameters, characteristics, and/or dimensions may vary across different moldable-member 207 of different (models and/or sizes of) sleep masks 100. In some embodiments, moldable-member 207 may be a solid cylindrical and elongate member. In some embodiments, the moldable-member 207 may be comprised of at least one wire. In some embodiments, the at least one wire (of moldable-member 207) may be made from at least one: metal and/or alloy. In some embodiments, moldable-member 207 may be comprise of at least one wire of at least one metal and/or of at least one alloy. In some embodiments, the metal and/or the alloy of moldable-member 207 may be selected from: aluminum, copper, steel, iron, tin, bronze, a portion thereof, combinations thereof, and/or the like. In some embodiments, the at least one wire may not be not operatively connected to any electronics. In some embodiments, the moldable-member 207 has no electronics. In some embodiments, the moldable-member 207 has no (or negligible) elasticity. In some embodiments, moldable-member 207 is not an elastic member. In some embodiments, the moldable-member 207 does not have parts that move with respect to each other.

In some embodiments, at least one main purpose and/or function of moldable-member 207 is to impart self-supporting characteristics to one or more of a given: sleep mask 100, front-exterior 101, first-portion (face-covering-portion) 201, face-facing-panel 301, second-portions (ear-loops) 203, portion thereof, combinations thereof, and/or the like.

In some embodiments, the only purpose and/or function of moldable-member 207 is to impart self-supporting characteristics to one or more of a given: sleep mask 100, front-exterior 101, first-portion (face-covering-portion) 201, face-facing-panel 301, second-portions (ear-loops) 203, portion thereof, combinations thereof, and/or the like.

In some embodiments, moldable-member 207 may be termed elongate-moldable-member 207.

In some embodiments, no parts and/or aspects of a given face mask 100 may be comprised of elastic members, such as, but not limited to, elastic straps and/or elastic strips. However, in some embodiments, fabric(s) and/or fabric covering(s) of face mask 100 may have elastic properties, but the ear-loops 203 and/or the moldable-member 207 may not be elastic.

Figure 3:
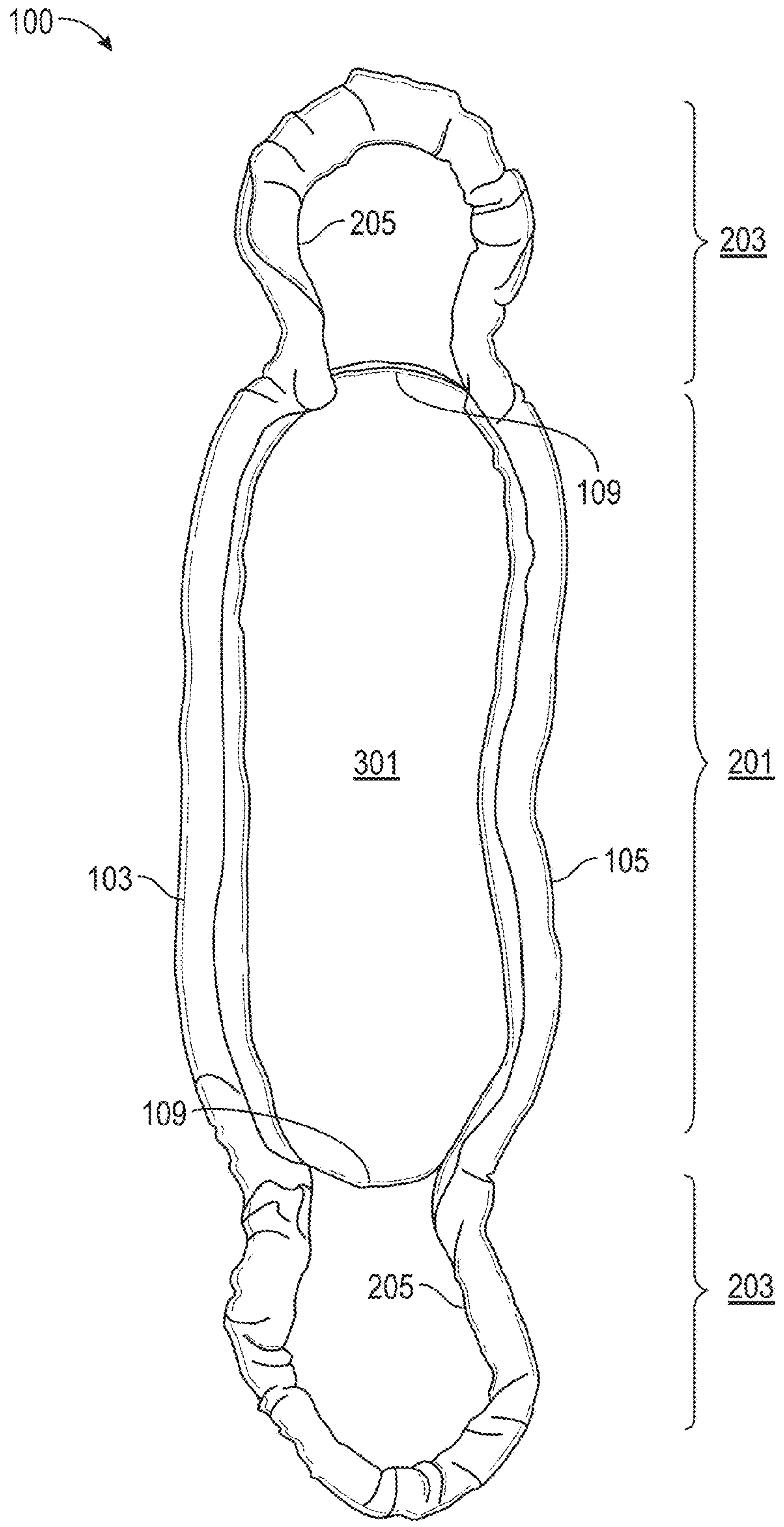
FIG. 3 shows a back (rear) view of the sleep mask from FIG. 1.

FIG. 3 shows a back (rear) view of sleep mask 100. FIG. 3 may be a mostly (substantially) opposing view for FIG. 2. In FIG. 3, the ear-loops 203 are shown extended away the first-portion 201 as is the scenario of FIG. 2. FIG. 2 also shows at least most of face-facing-panel 301. In some embodiments, face-facing-panel 301 may be opposing front-exterior 101. In some embodiments, when sleep mask 100 may be removably worn as intended on the face 1701 of the wearer 1700 (see e.g., FIG. 17), then face-facing-panel 301 may face the face 1701 of the wearer 1700. In some embodiments, when sleep mask 100 may be removably worn as intended on the face 1701 of the wearer 1700 (see e.g., FIG. 17), then at least some portions of face-facing-panel 301 may physically be touching at least some portion of the face 1701 of the wearer 1700. In some embodiments, face-facing-panel 301 may be an at least substantially (mostly) flat and/or planar member/surface. In some embodiments, face-facing-panel 301 may be comprised of at least one fabric. In some embodiments, the at least one fabric of face-facing-panel 301 may be one or more of: natural, synthetic, soft, flexible, pliable, bendable, foldable, non-elastic, washable, machine washable, cleanable, wipeable, sterilizable, portions thereof, combinations thereof, and/or the like. In some embodiments, the at least one fabric of face-facing-panel 301 may be the same or different from the at least one fabric of front-exterior 101, top-perimeter 103, bottom-perimeter 105, and/or ear-loop-covering 205. In some embodiments, face-facing-panel 301 may be have a 2D shape that is configured to removably cover over both eyes of the wearer 1700. In some embodiments, face-facing-panel 301 may be longer than wide, and wider than thick. In some embodiments, the width of face-facing-panel 301 may be variable along the length of face-facing-panel 301. In some embodiments, the width of face-facing-panel 301 may be wider at the portions of face-facing-panel 301 that may removably cover over the eyes of the wearer 1700 and narrower at the portion of face-facing-panel 301 that rests on or above a bridge of a nose 1705 of the wearer 1700. In some embodiments, the thickness of face-facing-panel 301 may be uniform (or at least mostly/substantially uniform). In some embodiments, face-facing-panel 301 may not be polygon shaped. In some embodiments, the 2D shape of face-facing-panel 301 may be the same, matching, similar, and/or complementary to the 2D shape front-exterior 101. In some embodiments, there may be no layers and/or material between face-facing-panel 301 and front-exterior 101 (other than air).

Note, moldable-member 207 does not run around an entire perimeter of the first-portion 201 in a manner that touches the entire perimeter of the first-portion 201. For example, and without limiting the scope of the present invention, the two (2) opposing side-perimeters 109 of the first-portion 201 are free of (without) moldable-member 207, i.e., moldable-member 207 is not attached to nor retained at the two (2) opposing side-perimeters 109 of the first-portion 201. See e.g., FIG. 3.

FIG. 4 shows a back (rear) view of sleep mask 100. FIG. 4 may be a mostly (substantially) opposing view for FIG. 1. In FIG. 4, the ear-loops 203 are shown folded over the first-portion 201 as is the scenario of FIG. 1. Comparing FIG. 1 and FIG. 4 to FIG. 2 and FIG. 3, also demonstrates the pliable, bendable, foldable, malleable, and/or sculptable nature of moldable-member 207 that is retained within top-perimeter 103, bottom-perimeter 105, and the two (2) ear-loop-coverings 205.

Figure 5:
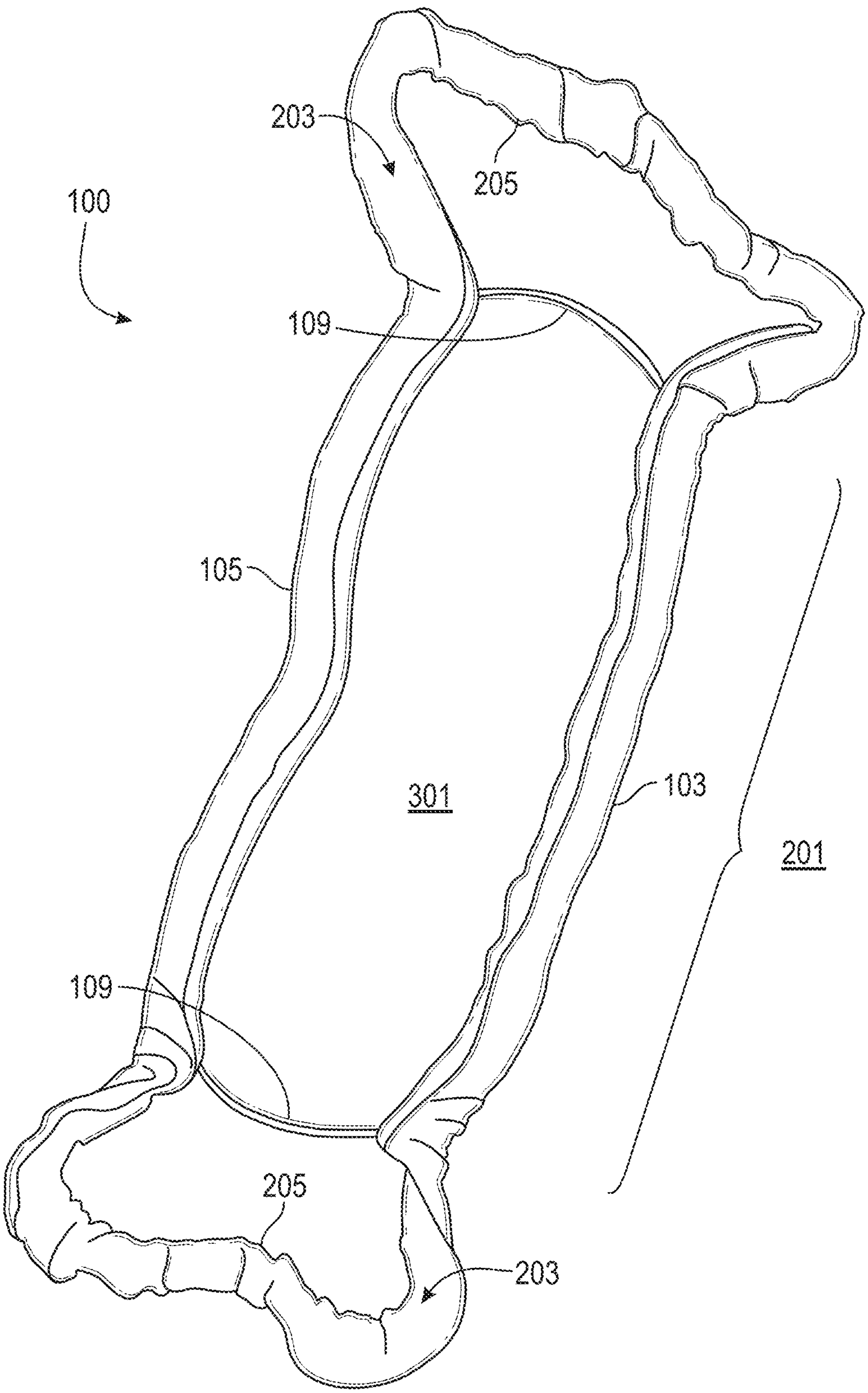
FIG. 5 shows a back (rear) view of the sleep mask from FIG. 1 with two (2) ear-loops shown bent into different shapes to demonstrate a pliable, bendable, foldable, malleable, and/or sculptable nature of a moldable-member of the sleep mask.

FIG. 5 shows a back (rear) view of sleep mask 100 with the two (2) ear-loops 203 shown bent into different shapes to further demonstrate the pliable, bendable, foldable, malleable, and/or sculptable nature of moldable-member 207.

Figure 6:
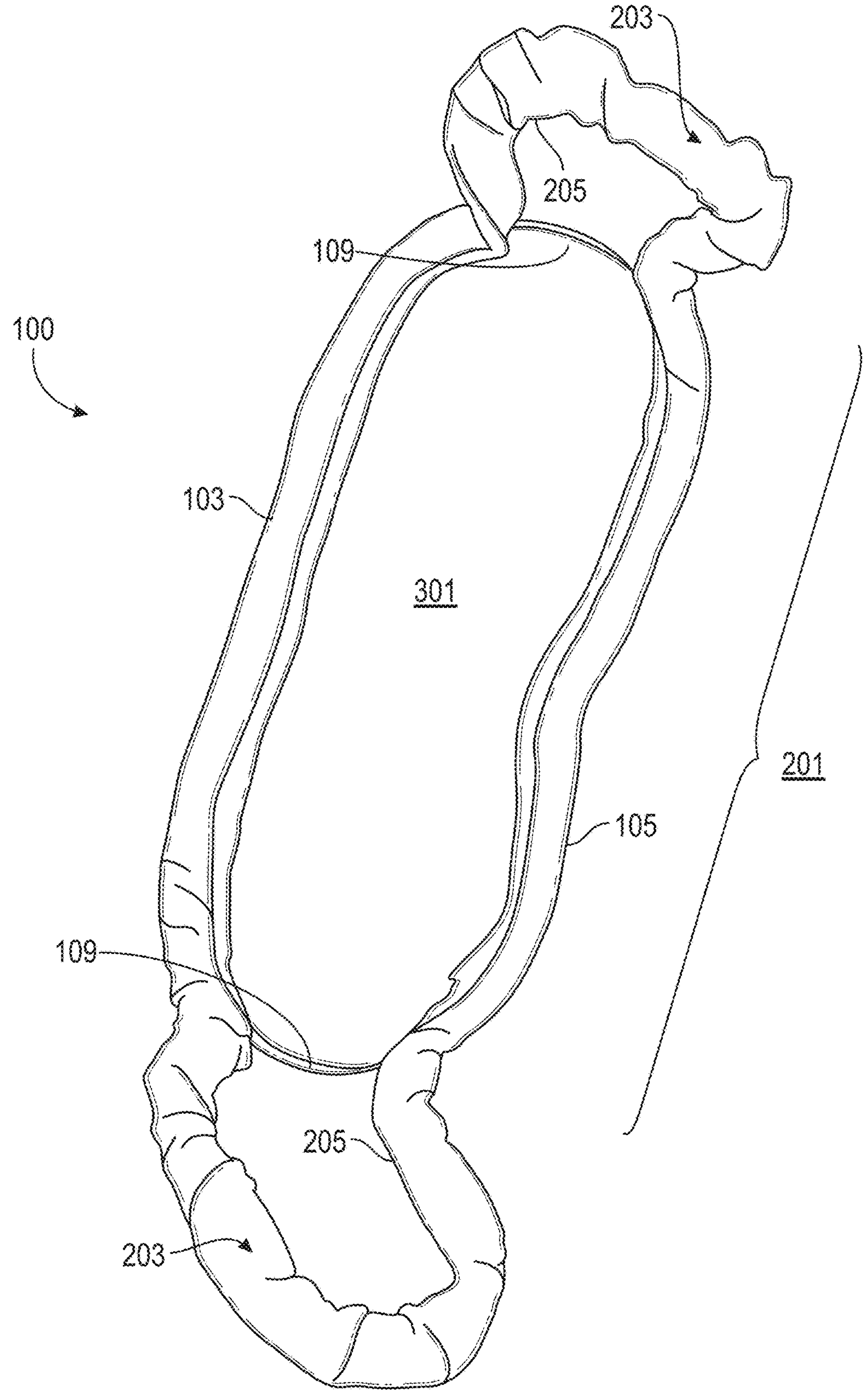
FIG. 6 shows a back (rear) perspective view of the sleep mask from FIG. 1 with the two (2) ear-loops shown bent into different shapes and extended away from the first-portion of the sleep mask to further demonstrate the pliable, bendable, foldable, malleable, and/or sculptable nature of the moldable-member.

FIG. 6 shows a back (rear) perspective view of sleep mask 100 with the two (2) ear-loops 203 shown bent into different shapes and extended away from the first-portion 201 to further demonstrate the pliable, bendable, foldable, malleable, and/or sculptable nature of moldable-member 207. The overall shape of sleep mask 100 shown in FIG. 6 is a shape that a given wearer 1700 might use when removably wearing sleep mask 100 on their face 1701. The shape of the two (2) ear-loop-coverings 205 shown in FIG. 6 are shapes may be comfortably removably worn on the ears 1703 of the wearer 1700.

Figure 7:
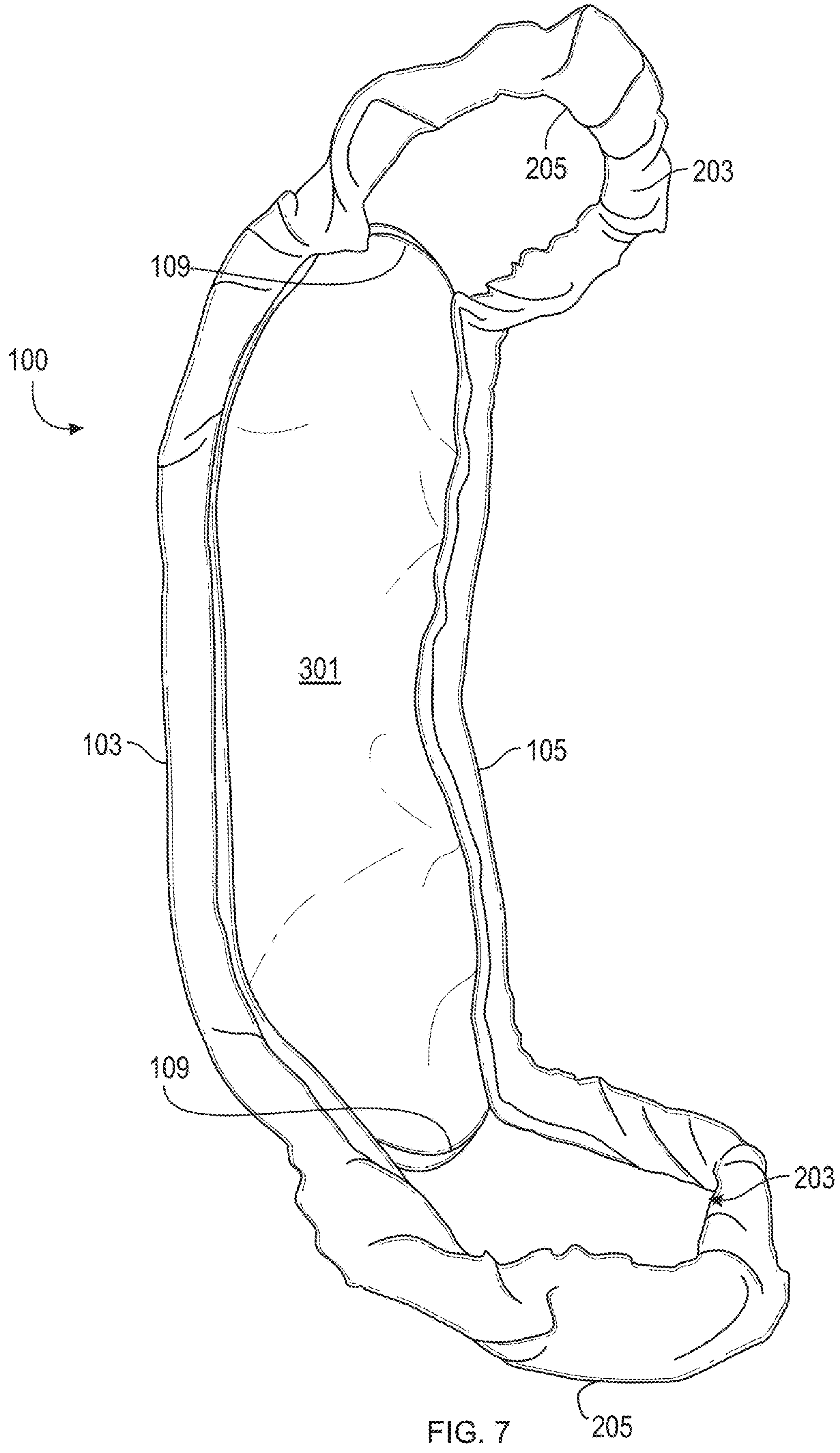
FIG. 7 shows a rear top perspective view of the sleep mask from FIG. 1 with the two (2) ear-loops shown bent into shape to be removably worn over the ears of a wearer of the sleep mask.

FIG. 7 shows a rear top perspective view of sleep mask 100 with the two (2) ear-loops 203 shown bent into shape to be removably worn over the ears 1703 of the wearer 1700.

Figure 8:
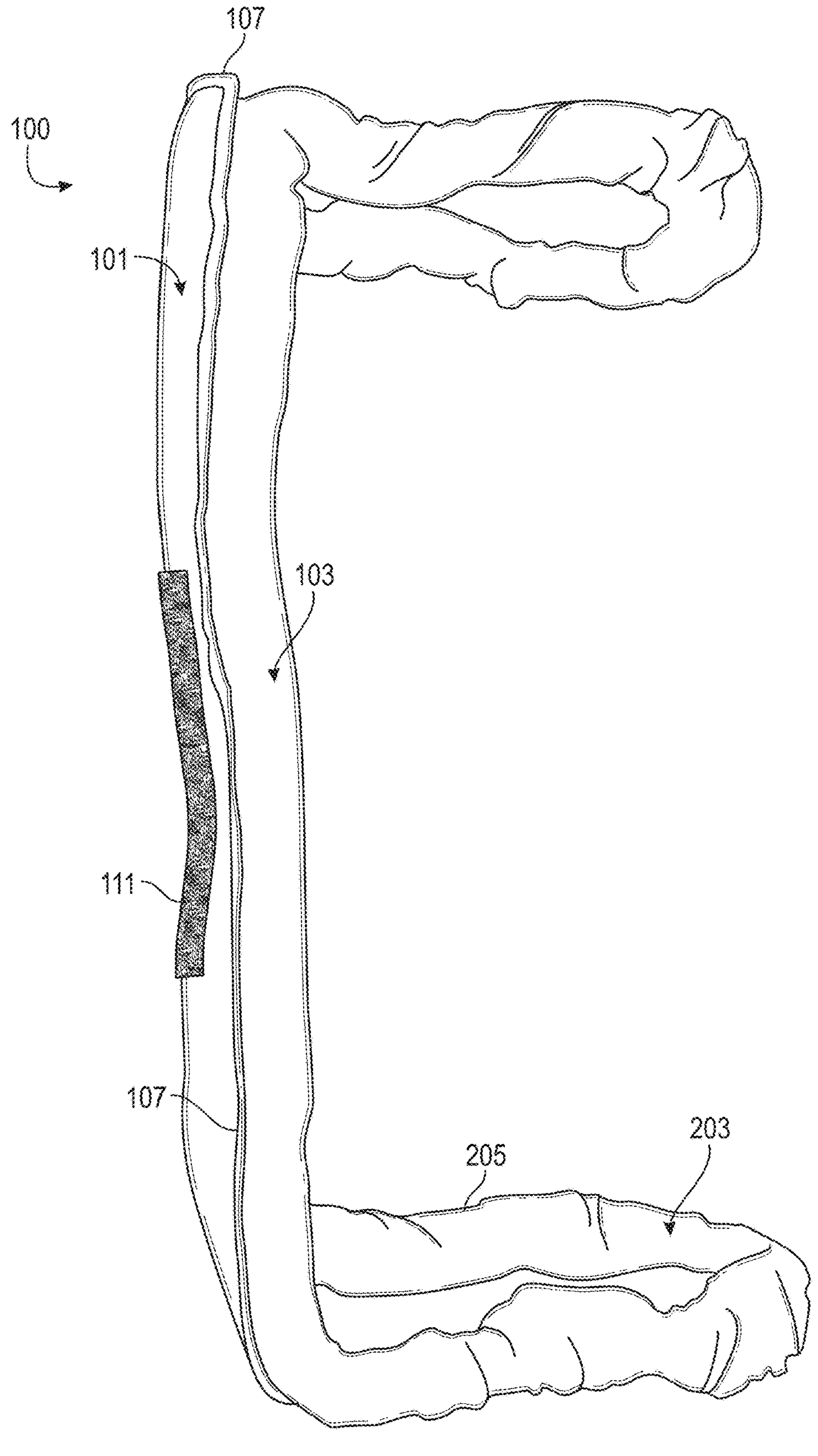
FIG. 8 shows a top perspective view of the sleep mask from FIG. 1, with the two (2) ear-loops shown bent into shape to be removably worn over the ears of the wearer.

FIG. 8 shows a top perspective view of sleep mask 100, with the two (2) ear-loops 203 shown bent into shape to be removably worn over the ears 1703 of the wearer 1700. The overall shape of sleep mask 100 shown in FIG. 8 may be similar to the shape of sleep mask 100 shown in FIG. 7.

Figure 9:
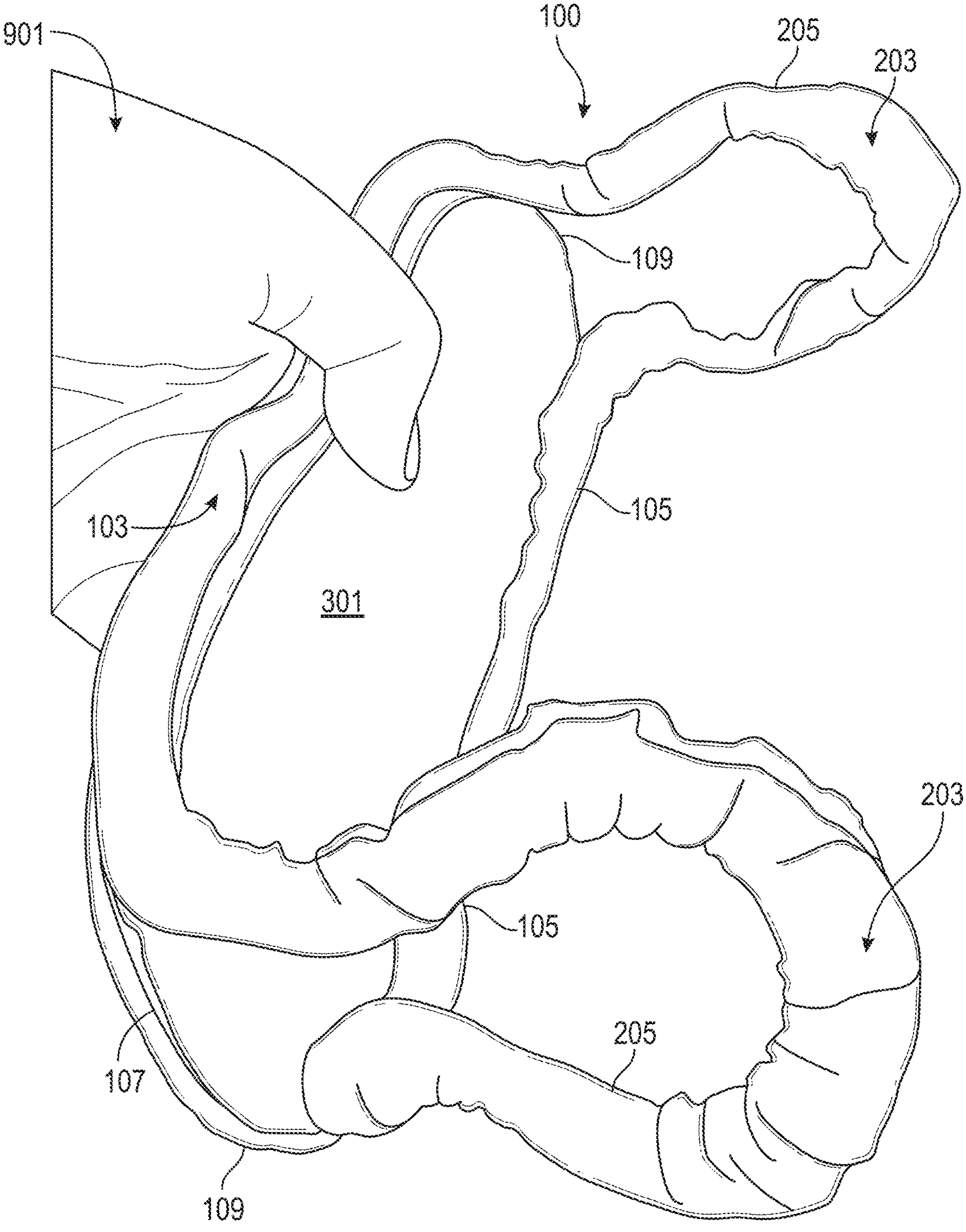
FIG. 9 shows a rear, top, and left-side perspective view of the sleep mask from FIG. 1 with the two (2) ear-loops shown bent into shape to be removably worn over the ears of the wearer.

FIG. 9 shows a rear, top, and left-side perspective view of sleep mask 100 with the two (2) ear-loops 203 shown bent into shape to be removably worn over the ears 1703 of the wearer 1700. The overall shape of sleep mask 100 shown in FIG. 9 may be similar to the shape of sleep mask 100 shown in FIG. 7 and/or in FIG. 8. A hand 901 of the wearer 1700 is shown in FIG. 9 holding the sleep mask 100. In FIG. 9, the hand 901 is the only object supporting sleep mask 100, yet the shape of the sleep mask 100 is retained (maintained), i.e., the shape of sleep mask 100 shown in FIG. 9 is not collapsing under its own weight. That is, moldable-member 207 is not pliable as to collapse under the weight of sleep mask 100.

Figure 10:
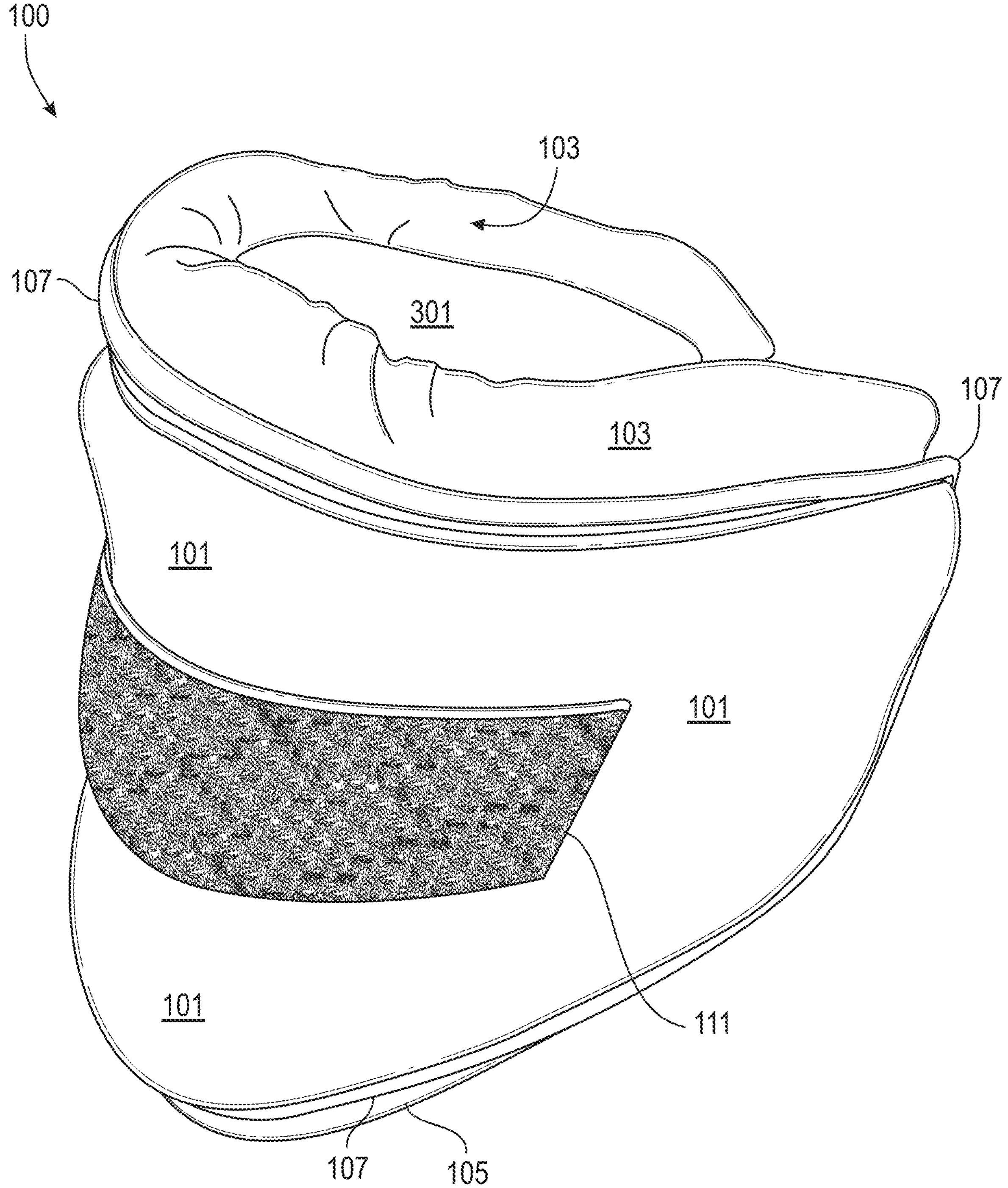
FIG. 10 shows a front exterior top and left-side perspective view of the sleep mask from FIG. 1 shown in a folded-up compact configuration, which further demonstrates the pliable, bendable, foldable, malleable, and/or sculptable nature of the moldable-member.

FIG. 10 shows a front exterior top and left-side perspective view of sleep mask 100 shown in a folded-up compact configuration, which further demonstrates the pliable, bendable, foldable, malleable, and/or sculptable nature of moldable-member 207.

Figure 11:
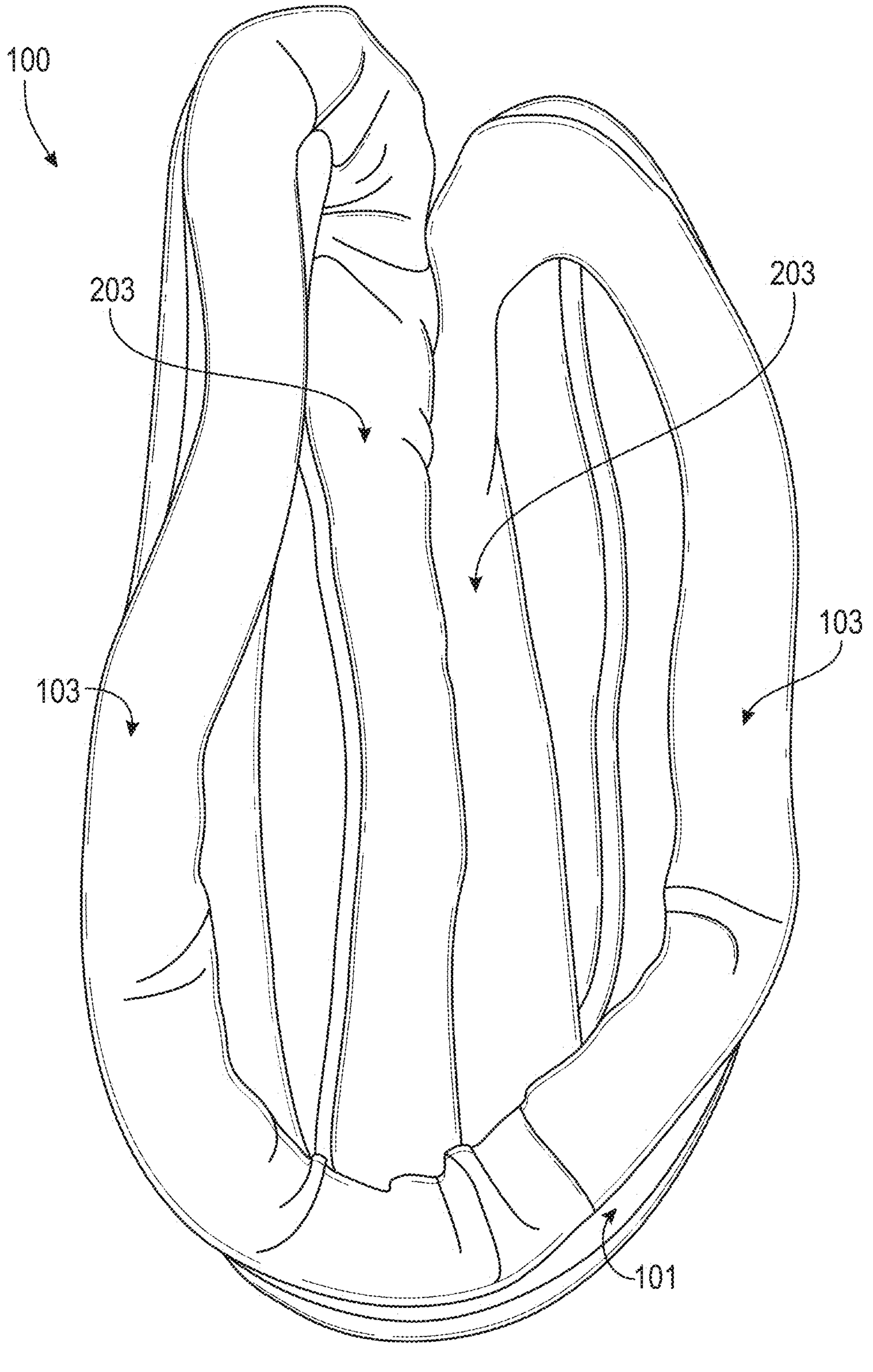
FIG. 11 shows another perspective view of the sleep mask from FIG. 1 shown in the same folded-up compact configuration of FIG. 10 to further demonstrate the pliable, bendable, foldable, malleable, and/or sculptable nature of the moldable-member.

FIG. 11 shows another perspective view of sleep mask 100 shown in the same folded-up compact configuration of FIG. 10 to further demonstrate the pliable, bendable, foldable, malleable, and/or sculptable nature of moldable-member 207. FIG. 11 shows the ear-loops 203 folded up to an interior of sleep mask 100 in this folded up compact configuration.

Figure 12:
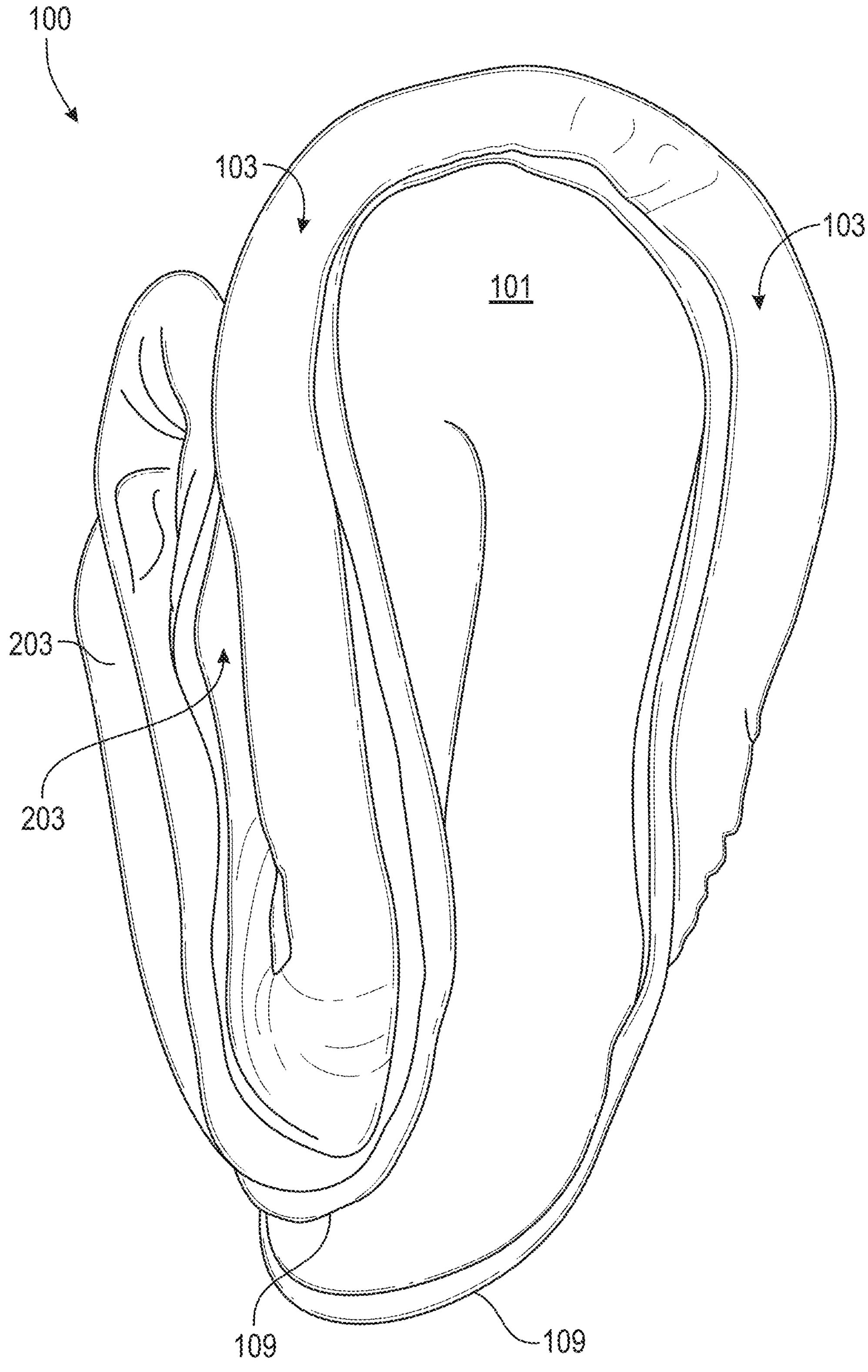
FIG. 12 shows a perspective view of the sleep mask from FIG. 1 shown in another (different) folded-up compact configuration, which further demonstrates the pliable, bendable, foldable, malleable, and/or sculptable nature of the moldable-member.

FIG. 12 shows a perspective view of sleep mask 100 shown in another (different) folded-up compact configuration, which further demonstrates the pliable, bendable, foldable, malleable, and/or sculptable nature of moldable-member 207. Note this folded up compact configuration of sleep mask 100 shown in FIG. 12 is essentially an opposite configuration to that shown in FIG. 10 and in FIG. 11. Here in FIG. 12 ear-loops 203 are folded to the outsides of this folded up compact configuration.

Figure 13:
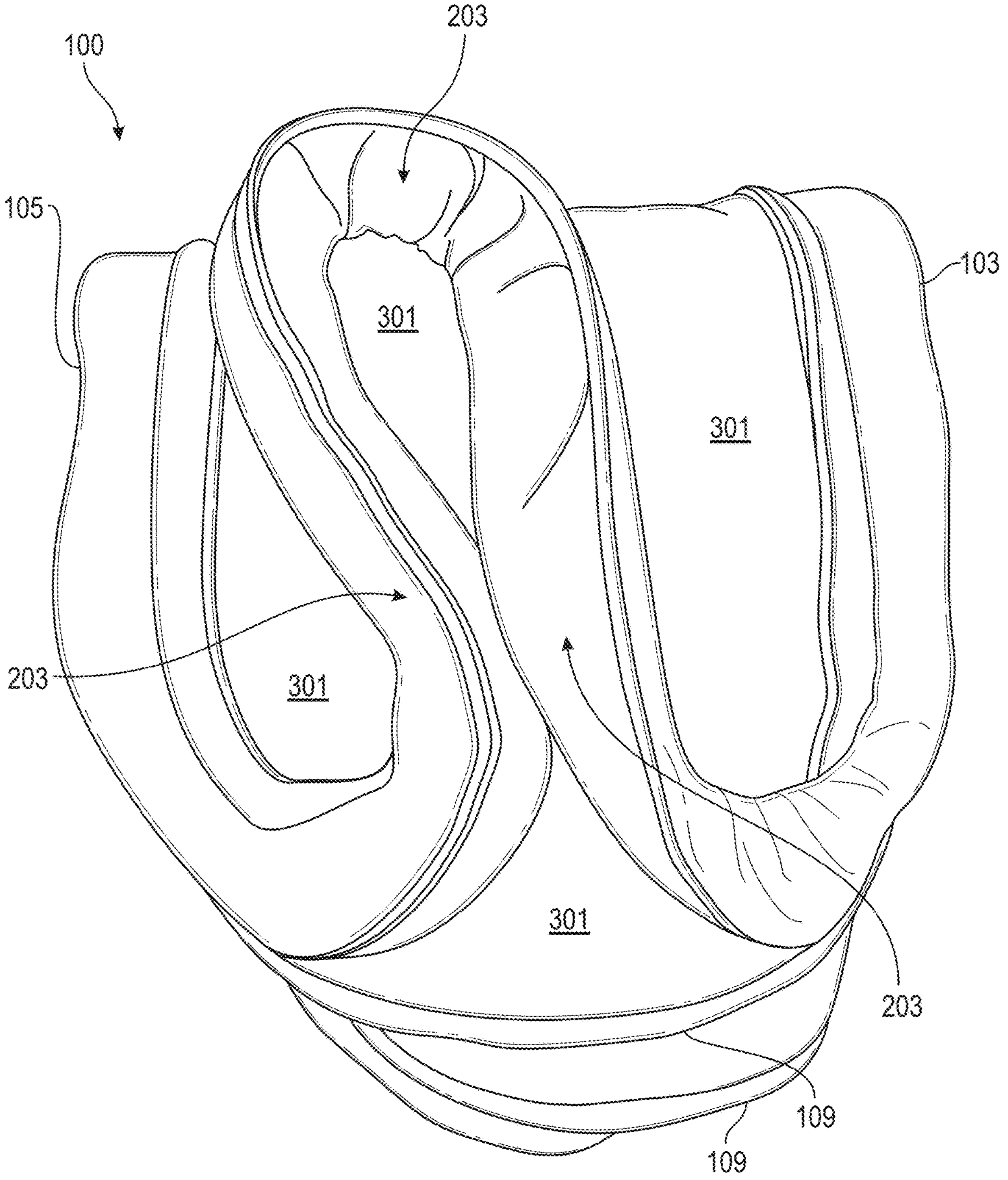
FIG. 13 shows another perspective view of the sleep mask from FIG. 1 shown in the same folded-up compact configuration of FIG. 12 to further demonstrate the pliable, bendable, foldable, malleable, and/or sculptable nature of the moldable-member.

FIG. 13 shows another perspective view of sleep mask 100 shown in the same folded-up compact configuration of FIG. 12 to further demonstrate the pliable, bendable, foldable, malleable, and/or sculptable nature of moldable-member 207. FIG. 13 shows the ear-loops 203 folded up on the outside folded up compact configuration.

Figure 14A:
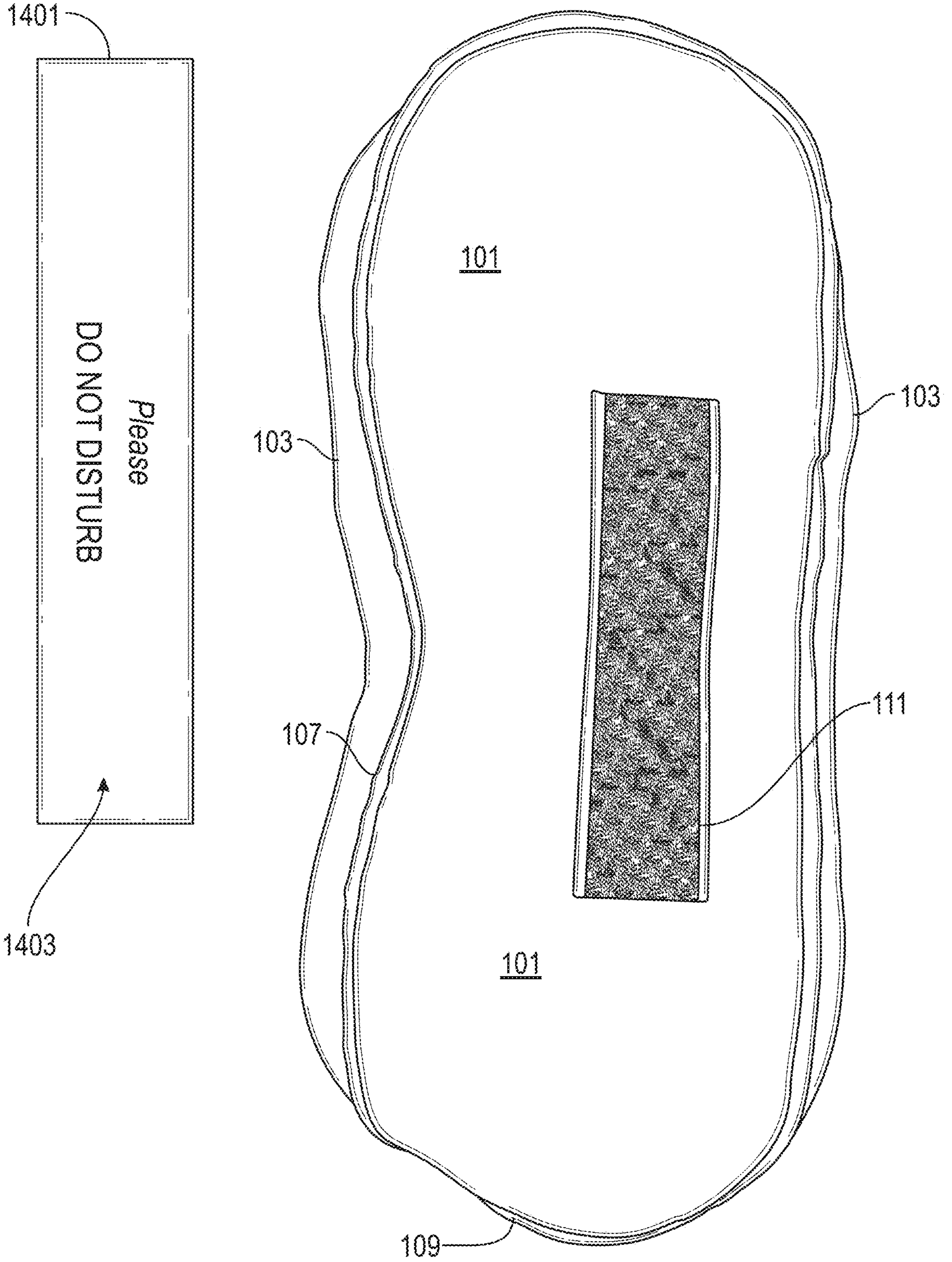
FIG. 14A shows the sleep mask from FIG. 1 from a front view (similar to FIG. 1) side by side with at least one removable label, with the label removed from the sleep mask.
Figure 14B:
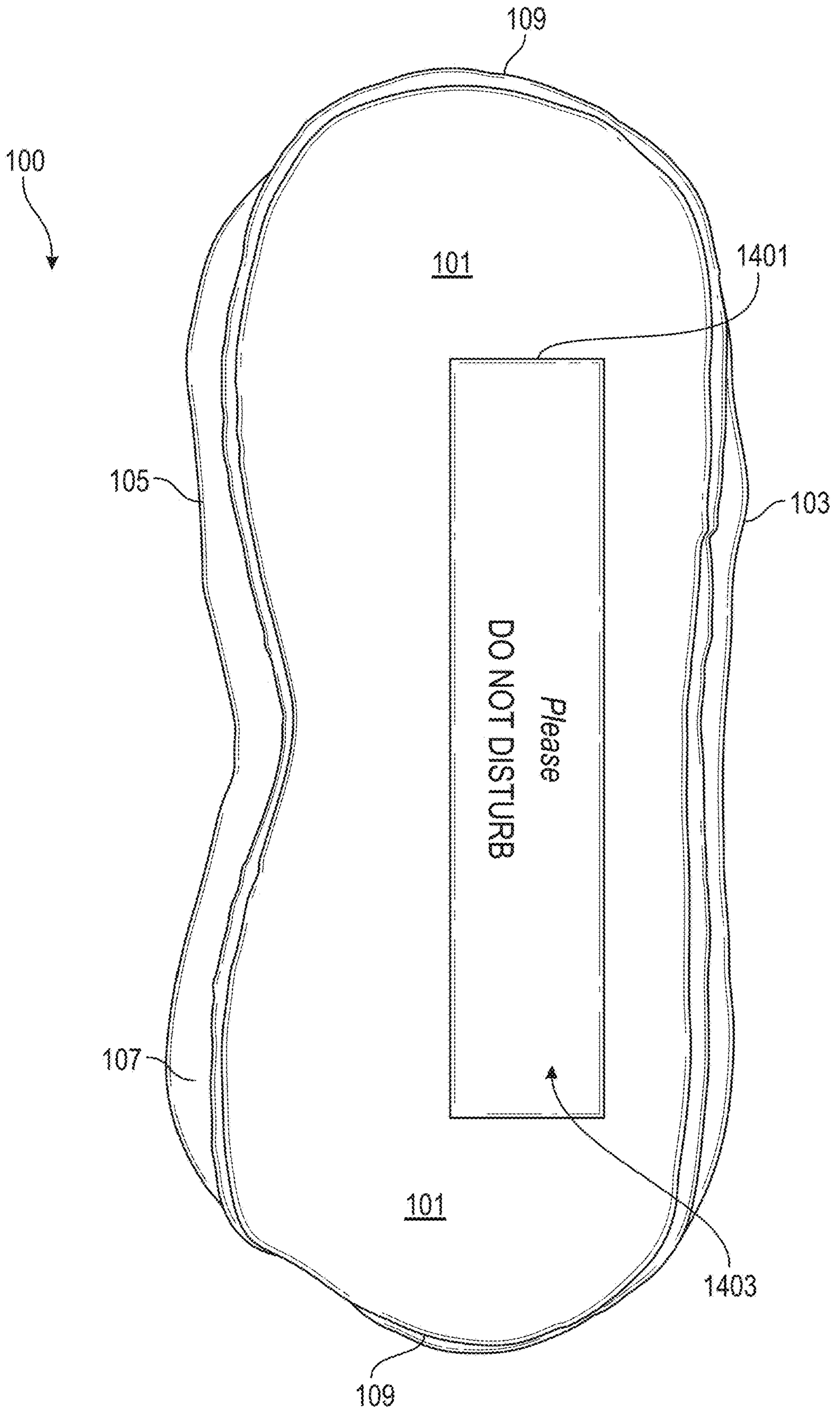
FIG. 14B shows the sleep mask from FIG. 14A, but now shown with the at least one label removably attached to a front-exterior (specifically to a label-attachment-means) of the sleep mask.

FIG. 14A shows a given sleep mask 100 from a front view (similar to FIG. 1) side by side with at least one label 1401. Whereas, FIG. 14B shows the given sleep mask 100 from the front view of FIG. 14A, but now with the at least one label 1401 shown removably attached to front-exterior 101 (specifically to label-attachment-means 111). In some embodiments, a given sleep mask 100 may comprise one or more removable label(s) 1401. In some embodiments, label 1401 may be longer than wide, and wider than thick. In some embodiments, label 1401 may be at least mostly (substantially) planar, flat, and/or flexible. In some embodiments, label 1401 may have a front exterior surface side and an opposing back (rear) surface side. In some embodiments, the front exterior surface side (and the back surface side) may have a predetermined 2D shape, such as, but not limited to, a polygon, a rectangle, an oval, a circle, a square, or a triangle. In some embodiments, label 1401 may be a label. In some embodiments, label 1401 may be a fabric label. In some embodiments, label 1401 may be a fabric label with a Nomax fastener backing, a Velcro fastener backing, a plurality of hooks fastener backing, a plurality of loops fastener backing, or like fabric fastener backing. In some embodiments, label 1401 may be a label with an attachment means on its back surface, such as, but not limited to, a Nomax fastener, a Velcro fastener, a plurality of hooks fastener, a plurality of loops fastener, or like fastener. In some embodiments, label 1401 may be configured to removably attached and detached from front-exterior 101 and/or from label-attachment-means 111.

Continuing discussing FIG. 14A and/or FIG. 14B, in some embodiments, label 1401 may be configured to present and/or provide visual messaging. In some embodiments, label 1401 may comprise messaging 1403 located on a front exterior of label 1401. In some embodiments, messaging 1403 may comprise visual content, such as, but limited to, text, word(s), letter(s), number(s), punctuation, graphics, character(s), symbol(s), artwork, logo(s), trademark(s), drawing(s), graph(s), scene(s), picture(s), photograph(s), font(s), portion thereof, combinations thereof, and/or the like. For example, and without limiting the scope of the present invention, messaging 1403 may convey and/or present a textual and/or word message of, "Please Do Not Disturb" or similar messages to convey that the wearer 1700 of the sleep mask 100 is resting, sleeping, and/or does not want to be disturbed/bothered. In some embodiments, messaging 1403 may in one or more colors, including but not limited to, neutrals, such as, white, black, gray, portion thereof, combinations thereof, and/or the like.

Figure 15:
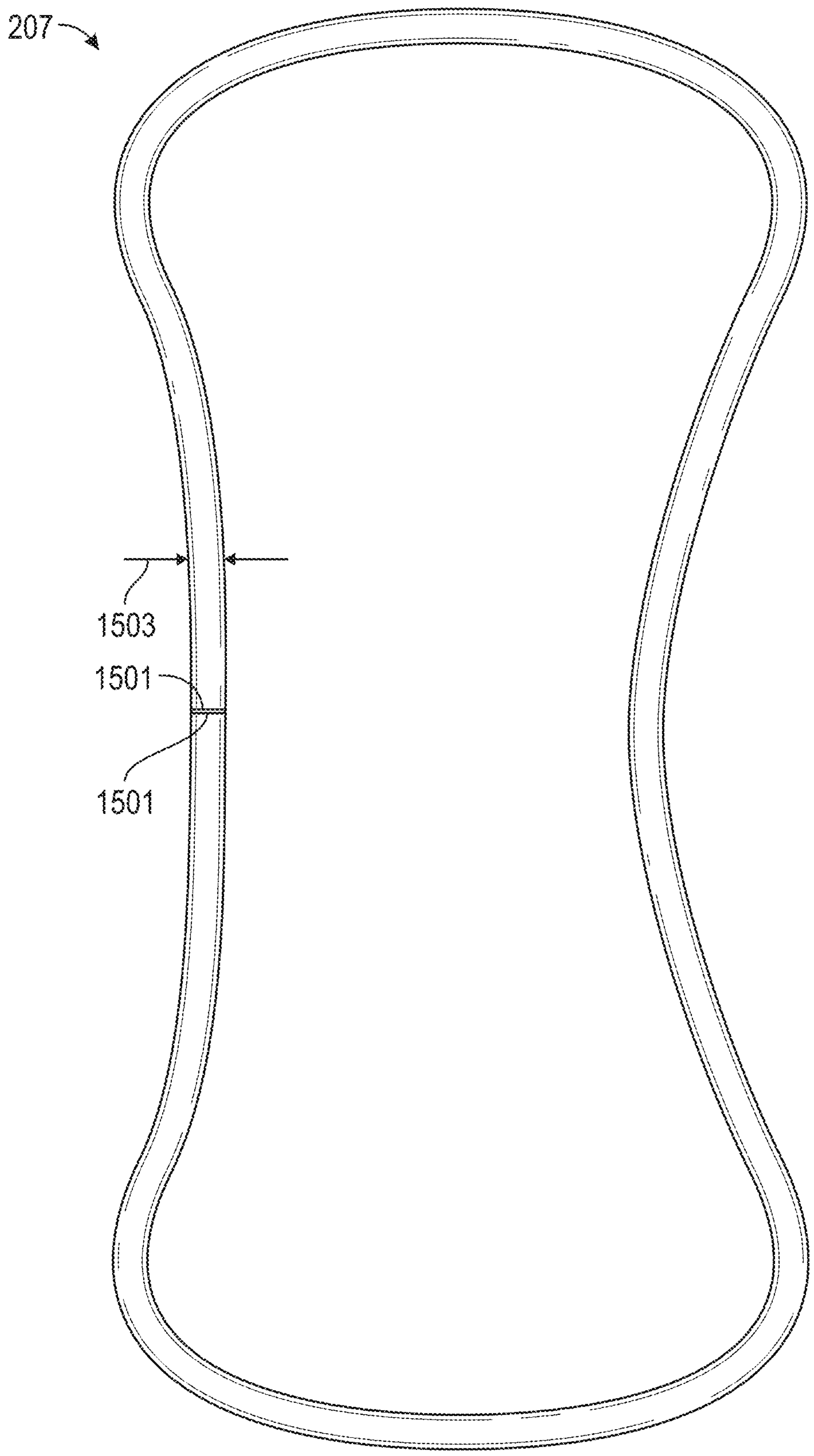
FIG. 15 shows a front (or rear) view of the moldable-member of the sleep mask, but without showing other elements of the sleep mask.

FIG. 15 shows a front (or rear) view of moldable-member 207 without showing other elements of sleep mask 100. In some embodiments, moldable-member 207 may be configured to be in a closed loop configuration with both of its terminal ends 1501 at least partially touching each other or proximate, adjacent, and/or near each other as shown in FIG. 15. In some embodiments, moldable-member 207 may be a mostly (substantially) tubular and/or cylindrical elongate member. In some embodiments, moldable-member 207 may be a mostly (substantially) flat and/or planar elongate member. In some embodiments, for a given size of sleep mask 100 moldable-member 207 may have a fixed, finite, non-variable, non-elastic, non-stretchy, and predetermined length, bound by the two (2) opposing terminal ends 1501 of moldable-member 207. In some embodiments, moldable-member 207 may be longer than first-portion 201 and/or longer than first-portion 201 elements. In some embodiments, other than threading, moldable-member 207 may be longer element of a given sleep mask 100. In some embodiments, when moldable-member 207 is assembled into a given sleep mask 100, none of moldable-member 207 may be exteriorly visible. In some embodiments, when moldable-member 207 is assembled into a given sleep mask 100, all of moldable-member 207 may be covered by fabric elements of sleep mask 100, such as, but not limited to, top-perimeter 103, bottom-perimeter 105, and the two (2) ear-loop-covers 205. Although FIG. 15 shows moldable-member 207 as a single (uniform) strand, in some embodiments, moldable-member 207 may be one or more strands of articulable, bendable, malleable, foldable, sculptable, and/or the like material. In some embodiments, moldable-member 207 may comprise one or more strands of articulable, bendable, malleable, foldable, sculptable, and/or the like elongate material. In some embodiments, strands of moldable-member 207 may be braided and/or twisted. In some embodiments, moldable-member 207 may be made at least mostly (substantially) from one or more metal(s) and/or metal alloy(s). In some embodiments, moldable-member 207 may be made at least mostly (substantially) from one or more of aluminum, copper, steel, iron, portions thereof, combinations thereof, and/or the like. In some embodiments, a given strand of moldable-member 207 may be anodized and/or coated (e.g., plastic coated, elastomer coated, and/or the like).

FIG. 15 also shows thickness 1503 (diameter 1503) of moldable-member 207. In some embodiments, thickness 1503 (diameter 1503) may be uniform, non-variable, non-elastic, non-stretchy, fixed, finite, and/or of a predetermined size. In some embodiments, a size of thickness 1503 (diameter 1503) may be selected from three (3) gauge to eighteen (18) gauge; whereas, in other embodiments, thickness 1503 (diameter 1503) may be another predetermined size (dimension).

Figure 16:
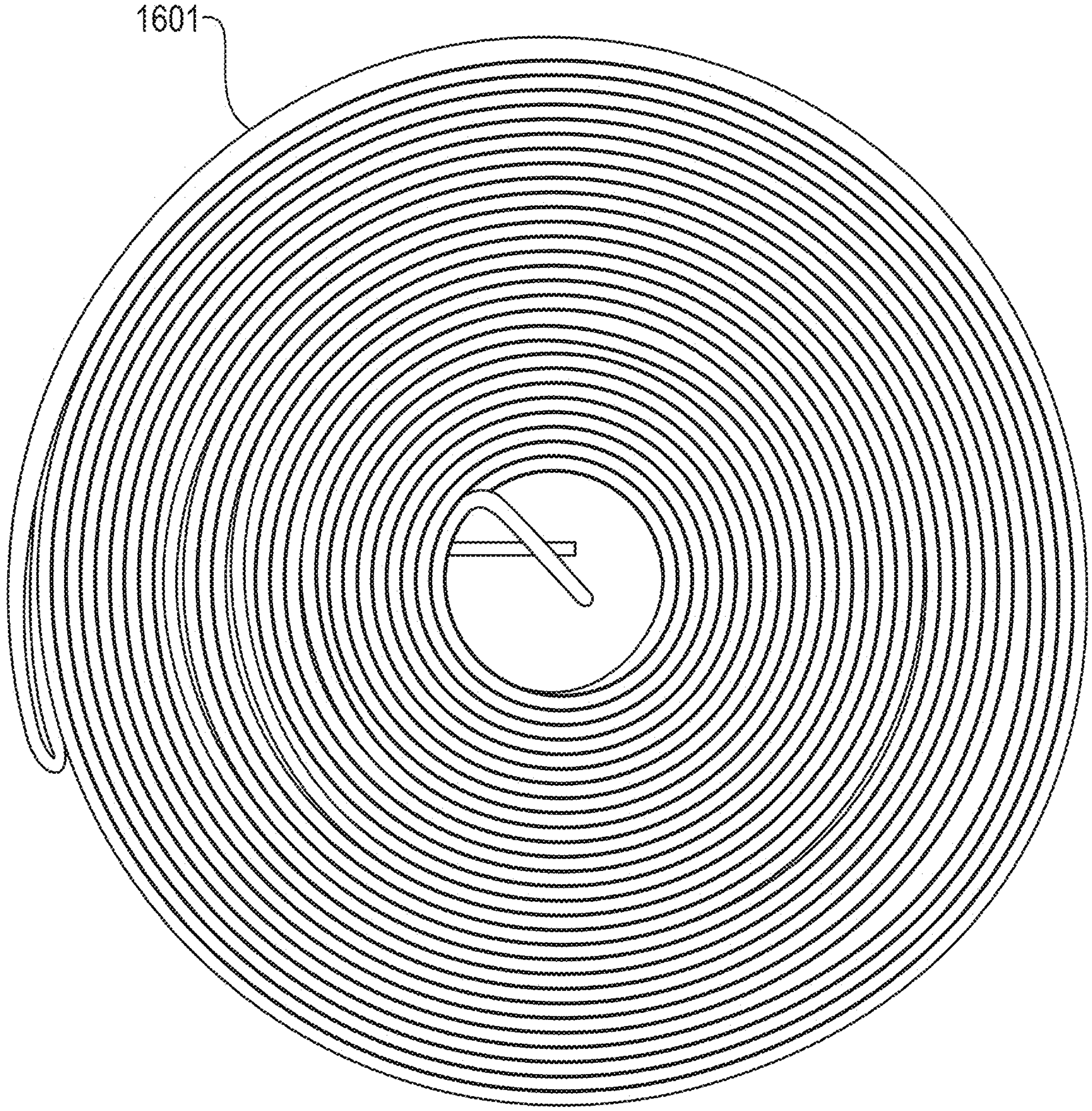
FIG. 16 shows as an example, a coil of an uncut moldable-member material, that may be cut to size to form one or more of the moldable-member(s) that are used in the assemblies of the sleep masks.

FIG. 16 shows as an example, a coil of uncut moldable-member 1601 material, that may be cut to size to form one or more moldable-member(s) 207. In some embodiments, uncut moldable-member 1601 may be the same as moldable-member 207, except that uncut moldable-member 1601 may be longer and/or not yet cut to smaller size(s) of moldable-member 207.

Figure 17:
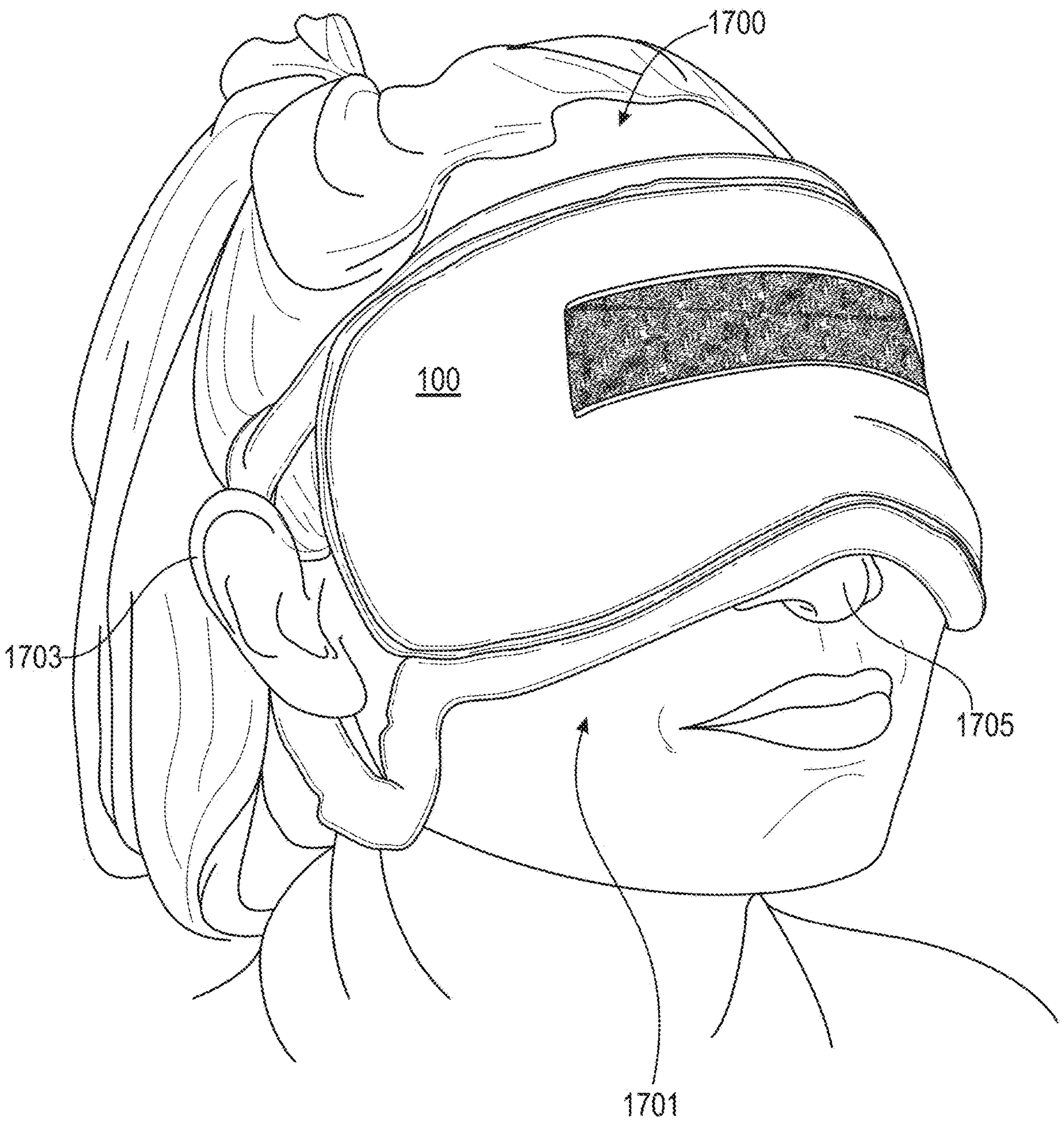
FIG. 17 shows a front right perspective view of the sleep mask from FIG. 1 being removably worn over a face of a given wearer.
Figure 18:
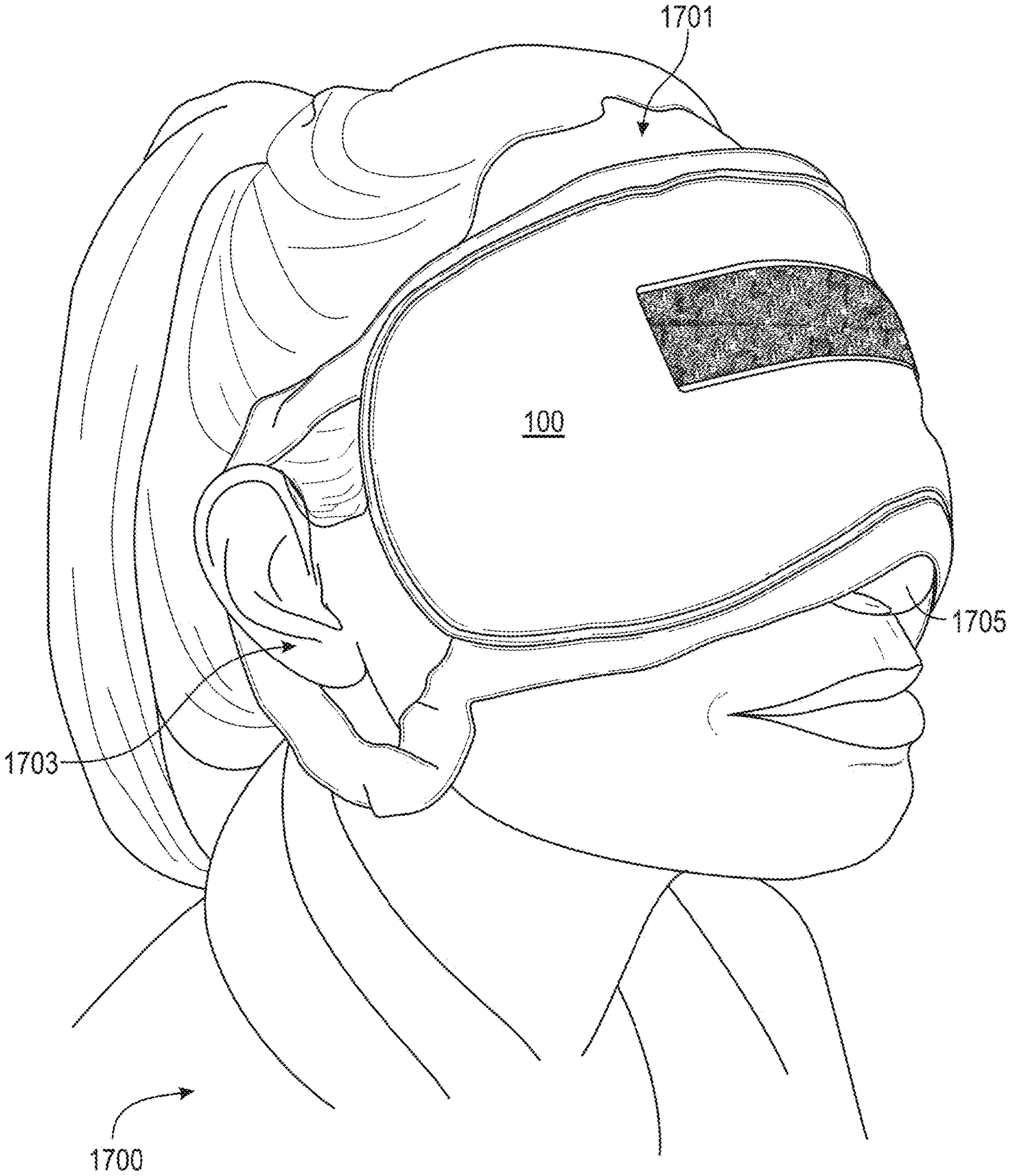
FIG. 18 shows a right perspective view of the sleep mask from FIG. 1 being removably worn over the face of the given wearer.

FIG. 17 and FIG. 18 show a given sleep mask 100 being removably worn over a face 1701 of a given wearer 1700. In some embodiments, when sleep mask 100 may be removably worn as intended, the first-portion 201 may removably cover over the eyes of the wearer 1700. In some embodiments, when sleep mask 100 may be removably worn as intended, the first-portion 201 may mold itself and conform to an exterior shape of the face 1701 of the wearer 1700 by virtue of moldable-member 207 and the flexible nature of the fabric(s) of sleep mask 100. In some embodiments, when sleep mask 100 may be removably worn as intended, the ear-loops 203 may be surrounding the ears 1703 of the wearer 1700. In some embodiments, when sleep mask 100 may be removably worn as intended, at least portions of the ear-loops 203 may be resting on top of the ears 1703 of the wearer 1700, which helps keep sleep mask 100 removably attached to the face 1701 of the wearer 1700 during intended use.

In some embodiments, when face mask 100 is being removably worn by a given wearer 1700, such as, but not limited to, as shown in FIG. 17 and/or in FIG. 18, no part of the face mask 100 covers over nostrils of nose 1705 nor of a mouth of that wearer 1700.

Figure 19:
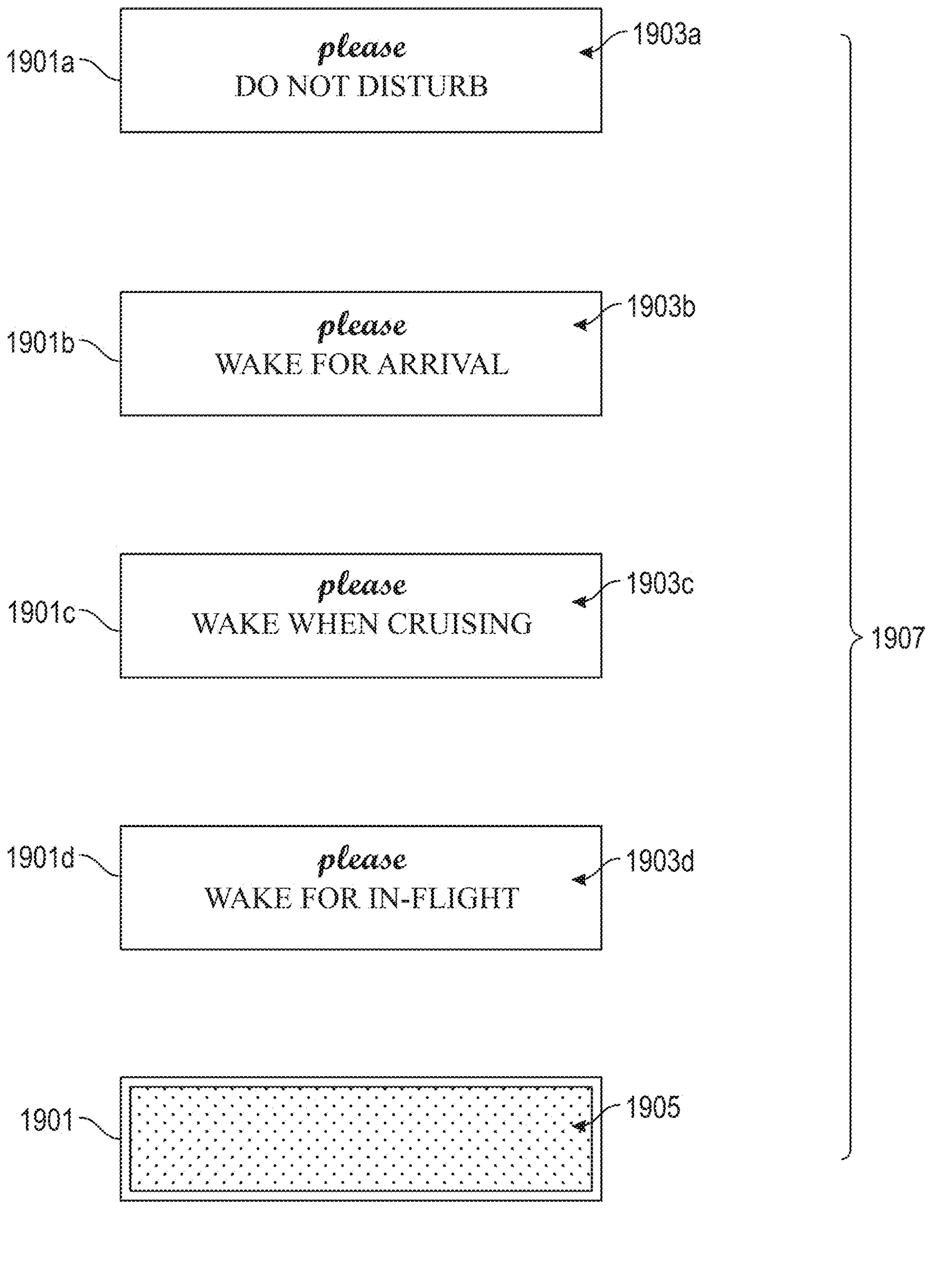
FIG. 19 shows a variety of different labels that may be removably attached from a given sleep mask, shown from a front side and from a back (rear) side.

FIG. 19 shows a variety of different labels 1901 (1401) that may be removably attached from/to a given sleep mask 100, shown from a front side and from a back (rear) side. FIG. 19 shows a label 1901*a* (1401) that may be removably attached from/to a given sleep mask 100. In some embodiments, label 1901*a* may comprise a front-of-label 1903*a* with messaging 1903*a* that states and/or reads, "Please DO NOT DISTURB" or the like. In some embodiments, the "Please" portion and the "DO NOT DISTURB" portion may be on different lines. In some embodiments, the "Please" portion may be in a cursive and/or in a handwriting style of font. In some embodiments, the "DO NOT DISTURB" portion may be in an all-caps style of font.

FIG. 19 shows a label 1901*b* (1401) that may be removably attached from/to a given sleep mask 100. In some embodiments, label 1901*b* may comprise a front-of-label 1903*b* with messaging 1903*b* that states and/or reads, "Please WAKE FOR ARRIVAL" or the like. In some embodiments, the "Please" portion and the "WAKE FOR ARRIVAL" portion may be on different lines. In some embodiments, the "Please" portion may be in a cursive and/or in a handwriting style of font. In some embodiments, the "WAKE FOR ARRIVAL" portion may be in an all-caps style of font.

FIG. 19 shows a label 1901*c* (1401) that may be removably attached from/to a given sleep mask 100. In some embodiments, label 1901*c* may comprise a front-of-label 1903*c* with messaging 1903*c* that states and/or reads, "Please WAKE WHEN CRUISING" or the like. In some embodiments, the "Please" portion and the "WAKE WHEN CRUISING" portion may be on different lines. In some embodiments, the "Please" portion may be in a cursive and/or in a handwriting style of font. In some embodiments, the "WAKE WHEN CRUISING" portion may be in an all-caps style of font.

FIG. 19 shows a label 1901*d* (1401) that may be removably attached from/to a given sleep mask 100. In some embodiments, label 1901*d* may comprise a front-of-label 1903*d* with messaging 1903*d* that states and/or reads, "Please WAKE FOR IN-FLIGHT" or the like. In some embodiments, the "Please" portion and the "WAKE FOR IN-FLIGHT" portion may be on different lines. In some embodiments, the "Please" portion may be in a cursive and/or in a handwriting style of font. In some embodiments, the "WAKE FOR IN-FLIGHT" portion may be in an all-caps style of font.

In some embodiments, when a subscript of "a," "b," "c," or "d" is not used with reference numeral 1901, then the reference may be to any label 1401 and/or label 1901 shown in the drawings.

In some embodiments, when a subscript of "a," "b," "c," or "d" is not used with reference numeral 1903, then the reference may be to any messaging 1403 and/or messaging 1903 shown in the drawings.

In some embodiments, the label(s) 1401, 1901, 1901*a*, 1901*b*, 1901*c*, and/or 1901*d* may be in one or more colors. In some embodiments, the messaging 1403, 1903, 1903*a*, 1903*b*, 1903*c*, and/or 1903*d* may be in one or more colors, fonts, font styles (such as, but not limited to, italics, bold, underlined, underscored, and/or the like), sizes, combinations thereof, and/or the like. In some embodiments, reference numerals 1401, 1901, 1901*a*, 1901*b*, 1901*c*, and/or 1901*d* may be used interchangeably. In some embodiments, reference numerals 1403, 1903, 1903*a*, 1903*b*, 1903*c*, and/or 1903*d* may be used interchangeably.

FIG. 19 also shows one back (rear) 1905 of a given label 1901. In some embodiments, the back (rear) 1905 of a given label 1901 may comprise attachment-means 1905. In some embodiments, attachment-means 1905 (on a rear or back of a given label 1901) may be removably attached to label-attachment-means 111 of a given sleep mask 100. In some embodiments, attachment-means 1905 and label-attachment-means 111 may be complementary to each other. In some embodiments, attachment-means 1905 may be selected from one or more of: a Nomax fastener, a Velcro fastener, a plurality of hooks fastener, a plurality of loops fastener, snaps, buttons, a zipper, a magnet, a ferrous metal, a magnetic strip, a ferrous metal strip, a clip, a fastener, a mechanical fastener, portions thereof, combinations thereof, and/or the like. In some embodiments, a type and/or style of attachment-means 1905 may be selected in order to be complementary with label-attachment-means 111. In some embodiments, a type and/or style of attachment-means 1905 and/or of label-attachment-means 111 may be selected in order to be complementary with each other to facilitate removable attachment of the given label from label-attachment-means 111 of a given sleep mask 100. In some embodiments, if attachment-means 1905 may be (or may comprise) at least one magnet (or magnetic strip), then label-attachment-means 111 may be (or may comprise) at least one other (different) magnet (or other different magnetic strip), so that attachment-means 1905 and label-attachment-means 111 may removably attach to each other. In some embodiments, if attachment-means 1905 may be (or may comprise) at least one magnet (or magnetic strip), then label-attachment-means 111 may be (or may comprise) at least one ferrous metal (or ferrous metal strip), so that attachment-means 1905 and label-attachment-means 111 may removably attach to each other. In some embodiments, if attachment-means 1905 may be (or may comprise) at least one ferrous metal (or ferrous metal strip), then label-attachment-means 111 may be (or may comprise) at least one magnet (or magnetic strip), so that attachment-means 1905 and label-attachment-means 111 may removably attach to each other.

FIG. 19 may show a plurality of labels 1907. In some embodiments, plurality of labels 1907 may comprise two or more of labels 1401, 1901, 1901*a*, 1901*b*, 1901*c*, and/or

1901*d*. In some embodiments, a kit and/or a system may comprise at least one sleep mask 100 and plurality of labels 1907. In some embodiments, such a kit and/or such a system may permit the user (the wearer) to utilize sleep mask 100 with a variety of different labels 1401, 1901, 1901*a*, 1901*b*, 1901*c*, and/or 1901*d*; with different messaging 1403, 1903, 1903*a*, 1903*b*, 1903*c*, and/or 1903*d*; such that the user (wearer) may convey different messages to others, at different times, by removing one given label and attaching another (different) given label to that particular sleep mask 100 (e.g., selected from the plurality of labels 1907), to accommodate different wants, desires, and/or needs of that user (wearer).

Figure 20:
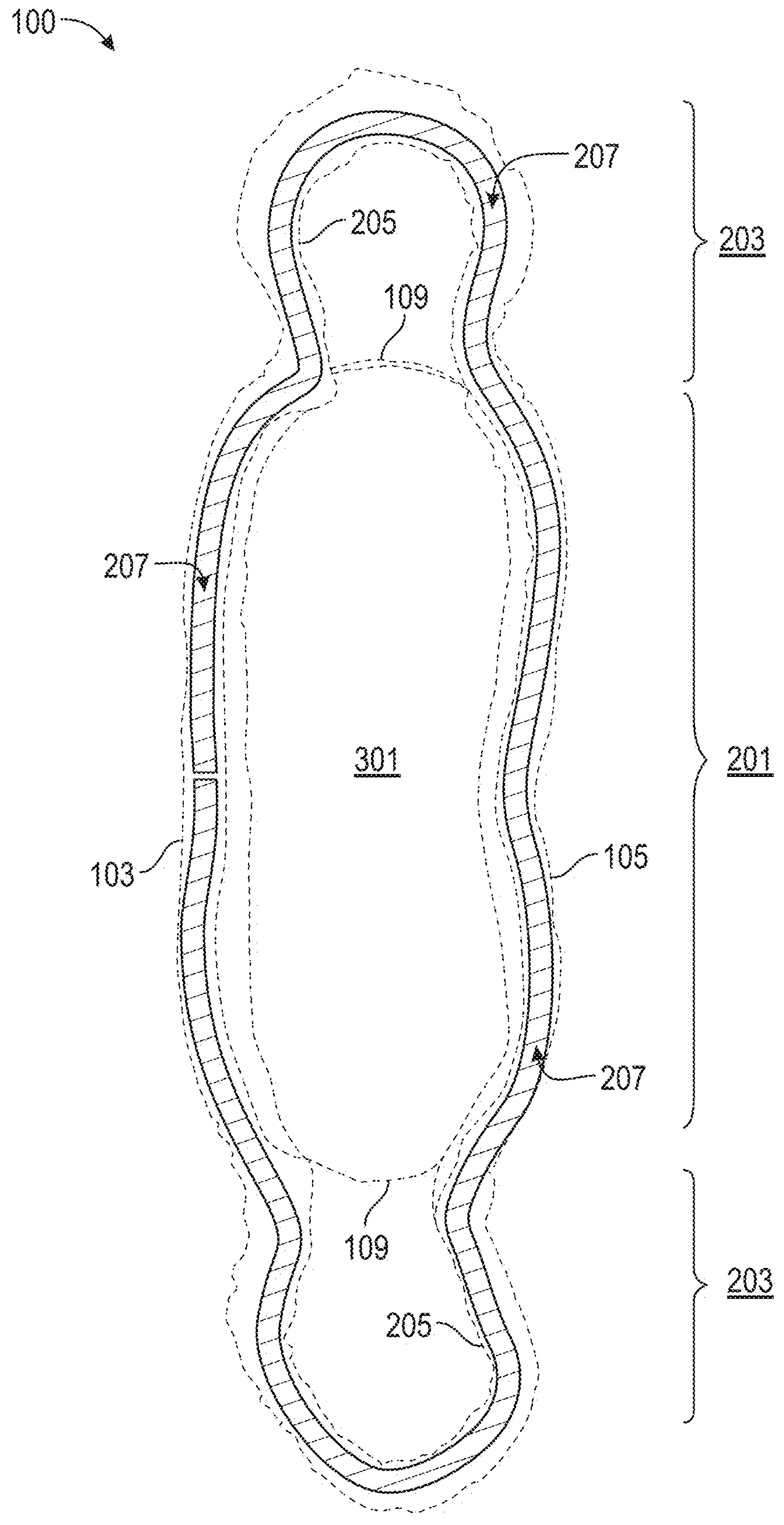
FIG. 20 shows a back (rear) view of the sleep mask from FIG. 1, similar to FIG. 3, except in FIG. 20, the exteriors of the sleep mask are shown in broken lines to indicate those exteriors are being shown as transparent so that a moldable-member, of that face mask, may be visible.

FIG. 20 shows a back (rear) view of sleep mask 100, similar to FIG. 3, except in FIG. 20 the exteriors of sleep mask 100 are shown in broken lines to indicate those exteriors are being shown as transparent so that moldable-member 207 may be visible. In actuality such transparency does not exist for the exteriors of sleep mask 100, i.e., FIG. 20 is merely to show moldable-member 207 in relation to its assembled sleep mask 100 as ordinarily moldable-member 207 is not visible from an exterior of its given assembled sleep mask 100.

Continuing discussing FIG. 20, in some embodiments, at least one elongate-moldable-member 207 may run in a loop from and along a bottom-perimeter 105 of the face-covering-portion 201, to and along a first ear-loop 203 selected from the two (2) ear-loops 203, to and along a top-perimeter 103 of the face-covering-portion 201, to and along a second ear-loop 203 selected from the two (2) ear-loops 203, and back to the bottom-perimeter 105 of the face-covering-portion 201. In some embodiments, this loop structure of at least one elongate-moldable-member 207 may be continuous (unbroken) or substantially (mostly) continuous. In some embodiments, this loop structure of at least one elongate-moldable-member 207 may have one or more breaks along a length of at least one elongate-moldable-member 207.

In some embodiments, sleep mask 100 may be referred to as mask 100, as travel mask 100, and/or the like. In some embodiments, mask 100 may comprise face-covering-portion 201, two (2) ear-loops 203, and at least one elongate-moldable-member 207. In some embodiments, face-covering-portion 201 may comprise at least one planar-member 101 and/or 301. In some embodiments, at least one planar-member 101 and/or 301 may be configured to cover over a portion of face 1701 of a wearer 1700 where eyes of the wearer 1700 are located when the mask 100 is being worn by the wearer 1700 as intended. In some embodiments, each ear-loop 203, selected from the two (2) ear-loops 203, may be configured for removable attachment to an ear 1703 of the wearer 1700 when the mask 100 is being worn by the wearer 1700 as intended. In some embodiments, each ear-loop 203, selected from the two (2) ear-loops 203, may extend out from face-covering-portion 201 in a manner such that the two (2) ear-loops 203 may be disposed opposite from each other. See e.g., FIG. 1, FIG. 2, FIG. 3, FIG. 17, FIG. 18, FIG. 20, and/or the like.

In some embodiments, at least one elongate-moldable-member 207 may run in a loop from and along a bottom-perimeter 105 of the face-covering-portion 201, to and along a first ear-loop 203 selected from the two (2) ear-loops 203, to and along a top-perimeter 103 of the face-covering-portion 201, to and along a second ear-loop 203 selected from the two (2) ear-loops 203, and back to the bottom-perimeter 105 of the face-covering-portion 201. See e.g., FIG. 20 that shows this loop structure of at least one elongate-moldable-member 207 within the context of an assembled mask 100. See also, FIG. 1, FIG. 2, FIG. 3, FIG. 17, FIG. 18, FIG. 20, and/or the like.

In some embodiments, the at least one elongate-moldable-member 207 may be bendable and/or (at least partially) self-supporting. In some embodiments, the bendable and/or the self-supporting characteristics of the at least one elongate-moldable-member 207 may permit each of the two (2) ear-loops 203 to be molded to exterior portions of ears 1703 of the wearer 1700. In some embodiments, the bendable and the self-supporting characteristics of the at least one elongate-moldable-member 207 may permit the face-covering-portion 201 to be molded to the portion of the face 1701 of the wearer 1700 where the eyes of the wearer 1700 are located. See e.g., FIG. 17 and FIG. 18.

In some embodiments, the top-perimeter 103 and the bottom-perimeter 105 may be separated from each other by side-perimeters 109 of the face-covering-portion 201, when the at least one planar-member 101 and/or 301 may be in a substantially flat and/or planar configuration. In some embodiments, the at least one elongate-moldable-member 207 does not run along either of the side-perimeters 109 of the face-covering-portion 201. In some embodiments, the at least one elongate-moldable-member 207 does not run along either of the side-perimeters 109 of the at least one planar-member 101 and/or 301. See e.g., FIG. 1, FIG. 2, FIG. 3, FIG. 20, and/or the like.

In some embodiments, the at least one elongate-moldable-member 207 does not run along interior and middle portions of the face-covering-portion 201 that are between the top-perimeter 103 and the bottom-perimeter 105. In some embodiments, the at least one elongate-moldable-member 207 does not run along interior and middle portions of the at least one planar-member 101 and/or 301 that are between the top-perimeter 103 and the bottom-perimeter 105. See e.g., FIG. 1, FIG. 2, FIG. 3, FIG. 20, and/or the like.

In some embodiments, the at least one elongate-moldable-member 207 may not run along portions of the face-covering-portion 201 that have a means 111 for attachment to a label 1401 and/or 1901. In some embodiments, the at least one elongate-moldable-member 207 may not run along portions of the at least one planar-member 101 that have a means 111 for attachment to a label 1401 and/or 1901. In some embodiments, the at least one elongate-moldable-member 207 may not physically touch nor be proximate to means 111 for attachment to a label 1401 and/or 1901. See e.g., FIG. 2, FIG. 14A, FIG. 14B, FIG. 20, and/or the like.

In some embodiments, the two (2) ear-loops 203 may not be elastic and/or may not utilize any elastic members, which may have a benefit of having better worn comfort for wearer 1700 as compared to prior art ear loops that use elastic to attach such ear loops to the ears of the wearer. In some embodiments, the at least one elongate-moldable-member 207 may not be elastic and/or may not utilize any elastic members.

In some embodiments, face-covering-portion 201 (or a portion thereof) may be opaque, non-transparent, non-translucent, a portion thereof, combinations thereof, and/or the like, with respect to eyesight of wearer 1700. In some embodiments, face-covering-portion 201 (or a portion thereof) may be at least substantially (mostly) opaque, non-transparent, non-translucent, a portion thereof, combinations thereof, and/or the like, with respect to eyesight of wearer 1700. In some embodiments, the at least one planar-member 101 and/or 301 (or a portion thereof) may be opaque, non-transparent, non-translucent, a portion thereof, combinations thereof, and/or the like, with respect to eyesight of wearer 1700. In some embodiments, the at least one planar-member 101 and/or 301 (or a portion thereof) may be at least substantially (mostly) opaque, non-transparent, non-translucent, a portion thereof, combinations thereof, and/or the like, with respect to eyesight of wearer 1700.

In some embodiments, mask 100 may be configured to operate as a sleep mask 100 (and/or as a travel mask 100), at least in part, because face-covering-portion 201 (or a portion thereof) and/or the at least one planar-member 101 and/or 301 may be (at least substantially) opaque, non-transparent, non-translucent, a portion thereof, combinations thereof, and/or the like, with respect to eyesight of wearer 1700; such that exterior visible light may be at least substantially (mostly) blocked from reaching the eyes of wearer 1700, when mask 100 is being worn as intended by wearer 1700, which in turn may be conductive for sleeping behavior of that wearer 1700. See e.g., FIG. 17, FIG. 18, and/or the like where when mask 100 is being removably worn as intended by wearer 1700 the eyes of wearer 1700 are not visible from an exterior observer.

In some embodiments, the face-covering-portion 201 may be longer than wide, and wider than thick. In some embodiments, the at least one planar-member 101 and/or 301 may be longer than wide, and wider than thick. See e.g., FIG. 1, FIG. 2, FIG. 3, FIG. 8, FIG. 20, and/or the like.

In some embodiments, the at least one planar-member 101 and/or 301 may be flexible and/or comprises at least one fabric (and/or may be at least substantially [mostly] made from at least one fabric).

In some embodiments, the face-covering-portion 201 may comprise a means 111 for attachment to a label 1401 and/or 1901. In some embodiments, the means 111 for attachment to the label 1401 and/or 1901 may be located on an exterior portion 101 of the face-covering-portion 201 that may be disposed away from the face 1701 of the wearer 1700 and not in direct physical contact with the face 1701 of the wearer 1700 when the mask 100 is being worn by the wearer 1700 as intended. In some embodiments, the exterior portion 101 that has this means 111 may located in a middle region of the face-covering-portion 201. In some embodiments, the means 111 for attachment to the label 1401 and/or 1901 may be selected from one or more of: a plurality of hooks fastener, a plurality of loops fastener, snaps, buttons, a zipper, a magnet, a ferrous metal, a magnetic strip, a ferrous metal strip, a clip, a fastener, and/or a mechanical fastener. In some embodiments, mask 100 may comprise at least one label 1401 and/or 1901. In some embodiments, the at least one label 1401 and/or 1901 may be configured for removable attachment to the means 111 for attachment. In some embodiments, at least one label 1401 and/or 1901 may comprise a plurality of labels 1907. In some embodiments, the label 1401 and/or 1901 may comprise messaging 1403 and/or 1903. See e.g., FIG. 1, FIG. 2, FIG. 14A, FIG. 14B, FIG. 17, FIG. 18, FIG. 19, and/or the like.

In some embodiments, no portion of the mask is configured to cover over nostrils of the wearer 1700 and/or of a mouth of the wearer 1700, when the mask 100 is being removably worn by the wearer 1700 as intended. See e.g., FIG. 14A, FIG. 14B, and/or the like.

In some embodiments, sleep mask 100 and/or its elements may be colored to match colors of various brands that might license and/or use sleep masks 100 for their customers, clients, and/or patients. In some embodiments, sleep mask 100 and/or its elements may be colored to match colors of trademark(s) and/or trade dress for various brands that might license and/or use sleep masks 100 for their customers, clients, and/or patients.

Fabric elements of sleep mask 100, such as, but not limited to, front-exterior 101, top-perimeter 103, bottom-perimeter 105, piping 107, side-perimeter 109, label-attachment-means 111, ear-loop-covering 205, face-facing-panel 301, portions thereof, combinations thereof, and/or the like, may be selected from one or more of: microsuede, neoprene, natural fabric(s), natural textile(s), cotton, wool, hemp, silk, cashmere, linen, Rayan, polypropylene, polyester, synthetic fabric(s), synthetic textile(s), a pre-existing fabric, a water proof fabric, a water resistance fabric, a wind proof fabric, a wind resistant fabric, a UV (ultraviolet) light proof fabric, a UV light resistant fabric, a UV blocking fabric, a visible light blocking fabric, a soft fabric, a hypoallergic fabric, portions thereof, combinations thereof, and/or the like.

Fabric elements of sleep mask 100, such as, but not limited to, front-exterior 101, top-perimeter 103, bottom-perimeter 105, piping 107, side-perimeter 109, label-attachment-means 111, ear-loop-covering 205, face-facing-panel 301, portions thereof, combinations thereof, and/or the like, may be attached to other such fabric elements by thread(s), stitching, welding, ultrasonic welding, solvent bonding, gluing, adhesives, portions thereof, combinations thereof, and/or the like.

In some embodiments, a given mask 100 may not comprise (may not have) one or more of the following: a head strap (e.g., a mask to head attachment means that passes around a rear of the wearer's head); an apron and/or a bib (e.g., a portion that hangs down over a mouth, chin, jaw, neck, or upper body portion of the wearer); a hood (e.g., a portion that covers over a top, sides, and/or rear of the head of the wearer); rigid exteriors; electronics; an opening in an ear-loop; a break in an ear-loop; an adjustment means for an ear-loop; a closure means in an ear-loop; a portion thereof; combinations thereof; and/or the like. In some embodiments, other than the label(s) 1401 and/or 1901, a given mask 100 may not comprise (may not have) any removable parts (components). In some embodiments, all portions of a given mask 100, except for label-to-mask attachment means (e.g., means 111), may be flexible, pliable, bendable, and/or the like. In some embodiments, messaging that may be on exteriors of label(s) 1401 and/or 1901, may not be directly on an exterior of front-exterior 101. In some embodiments, when a given mask 100 may be being removably worn by wearer 1700 as intended, then face-covering-portion 201 may simultaneously cover over both eyes, all the space between both of those eyes, and the bridge of the nose 1705; and may also cover over at least top (upper) portions of the facial cheeks of that wearer 1700. In some embodiments, when a given mask 100 may be being removably worn by wearer 1700 as intended, then face-covering-portion 201 may never cover over just a single eye of that wearer 1700 (if that wearer 1700 has two eyes).

Note with respect to the materials of construction, it is not desired nor intended to thereby unnecessarily limit the present invention by reason of such disclosure.

Note, while some portions of a human (e.g., wearer 1700) may be shown in some figures and discussed above, no human nor a portion thereof is claimed as part of the embodiments and/or inventions disclosed herein.

A sleep mask has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A mask that comprises:

a face-covering-portion that is comprised of at least one planar-member, wherein the at least one planar-member is configured to cover over a portion of a face of a wearer where eyes of the wearer are located when the mask is being worn by the wearer;

two ear-loops, wherein each ear-loop is configured for removable attachment to an ear of the wearer when the mask is being worn by the wearer, wherein each ear-loop extends out from the face-covering-portion in a manner such that the two ear-loops are disposed opposite from each other; and at least one elongate-moldable-member, wherein the at least one elongate-moldable-member is configured into a loop, wherein the loop runs from and along a bottom-perimeter of the face-covering-portion, to and along a first ear-loop selected from the two ear-loops, to and along a top-perimeter of the face-covering-portion, to and along a second ear-loop selected from the two ear-loops, and back to the bottom-perimeter of the face-covering-portion; wherein the at least one elongate-moldable-member is both bendable and self-supporting such that the at least one elongate-moldable-member has bendable characteristics and has self-supporting characteristics;

wherein the bendable characteristics and the self-supporting characteristics of the at least one elongate-moldable-member permit each of the two ear-loops to be molded to exterior portions of ears of the wearer;

wherein the bendable characteristics and the self-supporting characteristics of the at least one elongate-moldable-member permit the face-covering-portion to be molded to the portion of the face of the wearer where the eyes of the wearer are located.

2. The mask according to claim 1, wherein the top-perimeter and the bottom-perimeter are separated from each other by side-perimeters of the face-covering-portion, when the at least one planar-member is a substantially flat and/or planar configuration.

3. The mask according to claim 2, wherein the at least one elongate-moldable-member does not run along either of the side-perimeters of the face-covering-portion.

4. The mask according to claim 1, wherein the face-covering-portion has interior and middle portions that are between the top-perimeter and the bottom-perimeter, wherein the at least one elongate-moldable-member does not run along the interior and middle portions.

5. The mask according to claim 1, wherein the face-covering-portion has portions that have a means for attachment to a label, wherein the at least one elongate-moldable-member does not run along the portions of the face-covering-portion that have the means for attachment to the label.

6. The mask according to claim 1, wherein the two ear-loops are not elastic.

7. The mask according to claim 1, wherein the at least one elongate-moldable-member is not elastic.

8. The mask according to claim 1, wherein the at least one planar-member is opaque, non-transparent, and/or non-translucent.

9. The mask according to claim 1, wherein the mask is configured to operate as a sleep mask because the at least one planar-member is opaque, non-transparent, and/or non-translucent.

10. The mask according to claim 1, wherein the face-covering-portion is longer than wide, and wider than thick.

11. The mask according to claim 1, wherein the at least one planar-member is longer than wide, and wider than thick.

12. The mask according to claim 1, wherein the at least one planar-member is flexible and/or comprises at least one fabric.

13. The mask according to claim 1, wherein the face-covering-portion further comprises a means for attachment to a label.

14. The mask according to claim 13, wherein the face-covering-portion has an exterior-portion, wherein the exterior-portion is disposed away from the face of the wearer and not in direct physical contact with the face of wearer when the mask is being worn by the wearer, wherein the means for attachment to the label is located on the exterior-portion.

15. The mask according to claim 14, wherein the exterior-portion is located in a middle region of the face-covering-portion.

16. The mask according to claim 13, wherein the means for attachment to the label is selected from one or more of: a plurality of hooks fastener, a plurality of loops fastener, snaps, buttons, a zipper, a magnet, a ferrous metal, a magnetic strip, a ferrous metal strip, a clip, a fastener, and/or a mechanical fastener.

17. The mask according to claim 13, wherein the mask comprises the label, wherein the label is configured for removable attachment to the means for attachment.

18. The mask according to claim 17, wherein the label comprises a plurality of labels.

19. The mask according to claim 17, wherein the label comprises messaging.

20. The mask according to claim 1, wherein no portion of the mask is configured to cover over nostrils of the wearer and/or of a mouth of the wearer, when the mask is being removably worn by the wearer.

* * * * *